(12) United States Patent
Wachsman et al.

(10) Patent No.: US 10,525,407 B2
(45) Date of Patent: Jan. 7, 2020

(54) SYSTEMS, METHODS, AND DEVICES FOR DIRECT CONVERSION OF METHANE

(71) Applicant: University of Maryland, College Park, College Park, MD (US)

(72) Inventors: Eric D. Wachsman, Fulton, MD (US); Dongxia Liu, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 15/765,820

(22) PCT Filed: Oct. 6, 2016

(86) PCT No.: PCT/US2016/055818
§ 371 (c)(1),
(2) Date: Apr. 4, 2018

(87) PCT Pub. No.: WO2017/062663
PCT Pub. Date: Apr. 13, 2017

(65) Prior Publication Data
US 2018/0296974 A1     Oct. 18, 2018

Related U.S. Application Data

(60) Provisional application No. 62/300,338, filed on Feb. 26, 2016, provisional application No. 62/238,474, filed on Oct. 7, 2015.

(51) Int. Cl.
*C07C 2/76* (2006.01)
*B01D 71/02* (2006.01)
(Continued)

(52) U.S. Cl.
CPC .......... *B01D 53/32* (2013.01); *B01D 71/024* (2013.01); *B01J 8/0221* (2013.01); *B01J 8/0278* (2013.01);
(Continued)

(58) Field of Classification Search
None
See application file for complete search history.

(56) References Cited

U.S. PATENT DOCUMENTS 6,919,062 B1 *   7/2005   Vasileiadis .......... C07C 29/1518
                                                                 423/437.1
8,609,914 B2    12/2013   Tsou et al.
(Continued)

FOREIGN PATENT DOCUMENTS

WO      2002/070402 A2    9/2002

OTHER PUBLICATIONS

Guo et al., "Direct, nonoxidative conversion of methane to ethylene, aromatics, and hydrogen," *Science*, May 2014, 344: pp. 616-619.
(Continued)

*Primary Examiner* — Philip Y Louie
(74) *Attorney, Agent, or Firm* — Klarquist Sparkman, LLP

(57) ABSTRACT

Non-oxidative direct methane conversion (NDMC) to value-added products, such as $H_2$, $C_2$ hydrocarbons, and aromatics, occurs within a reactor heated to an elevated temperature. The reactor can have a first volume, where a feed gas including methane is provided, separated from a second volume, where a sweep gas is provided, by a dense thin film membrane supported on a porous wall. The thin film membrane is a mixed ionic-electronic permeable membrane that allows H2 generated in the first volume to be transported to the second volume for removal by (or reaction with) the sweep gas. A catalyst can be provided in or adjacent to the first volume. For example, the catalyst can be a metal doped quartz material (e.g., $Fe(c)SiO_2$) or a metal/zeolite material (e.g., Mo/ZSM5). Methane conversion and/or product selec-
(Continued)

tivity in the reactor can be manipulated by control of gas flow rates, reaction temperatures, and/or feed and sweep gas compositions.

24 Claims, 11 Drawing Sheets

(51) Int. Cl.
| | | |
|---|---|---|
| B01D 53/32 | (2006.01) | |
| B01J 8/06 | (2006.01) | |
| B01J 19/24 | (2006.01) | |
| B01J 8/02 | (2006.01) | |
| C01G 25/00 | (2006.01) | |
| C07C 2/84 | (2006.01) | |
| C04B 111/00 | (2006.01) | |
| C04B 35/626 | (2006.01) | |

(52) U.S. Cl.
CPC ........... *B01J 8/065* (2013.01); *B01J 19/2475* (2013.01); *C01G 25/006* (2013.01); *C07C 2/84* (2013.01); *C01P 2002/34* (2013.01); *C04B 35/6265* (2013.01); *C04B 2111/00801* (2013.01); *C04B 2235/3213* (2013.01); *C04B 2235/3217* (2013.01); *C04B 2235/449* (2013.01)

(56) References Cited

U.S. PATENT DOCUMENTS

| | | | |
|---|---|---|---|
| 9,527,044 B2 | 12/2016 | Wachsman et al. | |
| 9,932,280 B2 | 4/2018 | Bao et al. | |
| 2011/0040135 A1* | 2/2011 | Iaccino | C07C 2/76 585/412 |
| 2011/0084237 A1* | 4/2011 | Wachsman | B01D 67/0046 252/373 |
| 2012/0012467 A1 | 1/2012 | Tsou et al. | |
| 2014/0171708 A1* | 6/2014 | Chitta | C07C 2/76 585/417 |
| 2014/0336432 A1* | 11/2014 | Bao | C07C 2/84 585/417 |
| 2015/0028259 A1 | 1/2015 | Wachsman et al. | |
| 2016/0237002 A1* | 8/2016 | Vestre | C07C 2/76 |

OTHER PUBLICATIONS

International Search Report and Written Opinion, dated Feb. 2, 2017, for International Application No. PCT/US16/55818.
Alvarez-Galvan et al., "Direct methane conversion routes to chemicals and fuels," *Catalysis Today*, 2011, 171: pp. 15-23.
Ashcroft et al., "Selective oxidation of methane to synthesis gas using transition-metal catalysts," *Nature*, 1990, 344: pp. 319-321.
Cao et al., "Natural gas to fuels and chemicals: Improved methane aromatization in an oxygen-permeable membrane reactor," *Agnew. Chem.—Int. Edit.*, 2013, 52: pp. 13794-13797.
Caro, J., "Catalytic membrane reactors—lab curiosity or key enabling technology?," *Chemie Ingenieur Technik*, 2014, 86(11): pp. 1901-1905.
Deangelis et al., "Sol-gel synthesis of nanocrystalline fayalite ($Fe_2SiO_4$)," *American Mineralogist*, 2012, 97: pp. 653-656.
Gueret et al., "Methane pyrolysis: Thermodynamics," *Chemical Engineering Science*, 1997, 52(5): pp. 815-827.
Gupta et al., "Heterogeneous catalytic conversion of dry syngas to ethanol and higher alcohols on Cu-based catalysts," *ACS Catalysis*, 2011, 1: pp. 641-656.
Hamakawa et al., "Electrochemical hydrogen permeation in a proton-hole mixed conductor and its application to a membrane reactor," *Journal of the Electrochemical Society*, 1994, 141(7): pp. 1720-1725.
Hickman et al., "Production of syngas by direct catalytic oxidation of methane," *Science*, 1993, 259(5093): pp. 343-346.
Horn et al., "Methane activation by heterogeneous catalysis," *Catal. Lett.*, 2015, 145: pp. 23-39.
Iliuta et al., "Methane nonoxidative aromatization over Ru—Mo/HZSM-5 at temperatures up to 973 K in a palladium-silver/stainless steel membrane reactor," *Ind. Eng. Chem. Res*, 2003, 42: pp. 323-330.
Iliuta et al., "Methane nonoxidative aromatization over Ru—Mo/HZSM-5 in a membrane catalytic reactor," *Ind. Eng. Chem. Res.*, 2002, 41: pp. 2371-2378.
Ismagilov et al., "Direct conversion of methane on Mo/ZSM-5 catalysts to produce benzene and hydrogen: achievements and perspectives," *Energy & Environmental Science*, 2008, 1: pp. 526-541.
Keller et al., "Synthesis of ethylene via oxidative coupling of methane. 1. Determination of active catalysts," *Journal of Catalysis*, 1982, 73: pp. 9-19.
Lee et al., "Oxidative coupling of methane to higher hydrocarbons," *Catal. Rev.*, 1988, 30: pp. 249-280.
Li et al., "Carbon dioxide reforming of methane in $SrCe_{0.7}Zr_{0.2}Eu_{0.1}O_{3-\delta}$ proton conducting membrane reactor," *International Journal of Hydrogen Energy*, 2012, 37: pp. 19125-19132.
Li et al., "Design and optimization of catalysts and membrane reactors for the non-oxidative conversion of methane," *Chemical Engineering Science*, 2002, 57: pp. 4595-4604.
Li et al., "Hydrogen permeation through thin supported $SrCe_{0.7}Zr_{0.2}Eu_{0.1}O_{3-\delta}$ membranes; dependence on flux on defect equilibria and operating conditions," *Journal of Membrane Science*, 2011, 381: pp. 126-131.
Li et al., "Reaction-transport simulations of non-oxidative methane conversion with continuous hydrogen removal—homogeneous-heterogeneous reaction pathways," *Chemical Engineering Science*, 2001, 56: pp. 1869-1881.
Li et al., "$SrCe_{0.7}Zr_{0.2}Eu_{0.1}O_3$-based hydrogen transport water gas shift reactor," *International Journal of Hydrogen Energy*, 2012, 37: pp. 16006-16012.
Liu et al., "Methane coupling using catalytic membrane reactors," *Catalysis Reviews*, 2001, 43(1&2): pp. 147-198.
Natesakhawat et al., "Improved benzene production from methane dehydroaromatization over Mo/HZSM-5 catalysts via hydrogen-permselective palladium membrane reactors," *Catalysis Science & Technology*, 2015, 5: pp. 5023-5036.
Oh et al., "Hydrogen permeation through thin supported $SrZr_{0.2}Ce_{0.8-x}Eu_xO_{3-\delta}$ membranes," *Journal of Membrane Science*, 2009, 345: pp. 1-4.
Pakhare et al, "A review of dry ($CO_2$) reforming of methane over noble metal catalysts," *Chem. Soc. Rev.*, 2014, 43: pp. 7813-7837.
Rival et al., "Oxygen-free methane aromatization in a catalytic membrane reactor," *Ind. Eng. Chem. Res.*, 2001, 40: pp. 2212-2219.
Song et al., "A clue to exploration of the pathway of coke formation on Mo/HZSM-5 catalyst in the non-oxidative methane dehydroaromatization at 1073K," *Applied Catalysis A: General*, 2014, 482: pp. 387-396.
Spivey et al., "Catalytic aromatization of methane," *Chem. Soc. Rev.*, 2014, 43: pp. 792-803.
Tonkovich et al., "Enhanced $C_2$ yields from methane oxidative coupling by means of a separative chemical reactor," *Science*, 1993, 262: pp. 221-223.
Wang et al., "Catalytic conversion of methane to benzene over Mo/ZSM-5," *Topics in Catalysis*, 1996, 3: pp. 289-297.
Wang et al., "Characterization of a Mo/ZSM-5 catalyst for the conversion of methane to benzene," *Journal of Catalysis*, 1997, 169: pp. 347-358.
Wang et al., "Dehydrogenation and aromatization of methane under nonoxidizing conditions," *Catalysis Letters*, 1993, 21: pp. 35-41.
Weckhuysen et al., "Conversion of methane to benzene over transition metal ion ZSM-5 zeolites—II. Catalyst characterization of x-ray photoelectron spectroscopy," *Journal of Catalysis*, 1998, 175: pp. 347-351.

(56) References Cited

OTHER PUBLICATIONS

Wu et al., "Spatial distribution and catalytic performance of metal-acid sites in Mo/MFI catalysts with tunable meso-/microporous lamellar zeolite structures," *Journal of Catalysis*, 2015, 323: pp. 100-111.

Wu et al., "Textural and catalytic properties of Mo loaded hierarchical meso-/microporous lamellar MFI and MWW zeolites for direct methane conversion," *Applied Catalysis A: General*, 2014, 470: pp. 344-354.

Yoon et al., "Fabrication of thin-film $SrCe_{0.9}Eu_{0.1}O_{3-\delta}$ hydrogen separation membranes on $Ni-SrCeO_3$ porous tubular supports," *Journal of the American Ceramic Society*, 2009, 92(8): pp. 1849-1852.

\* cited by examiner

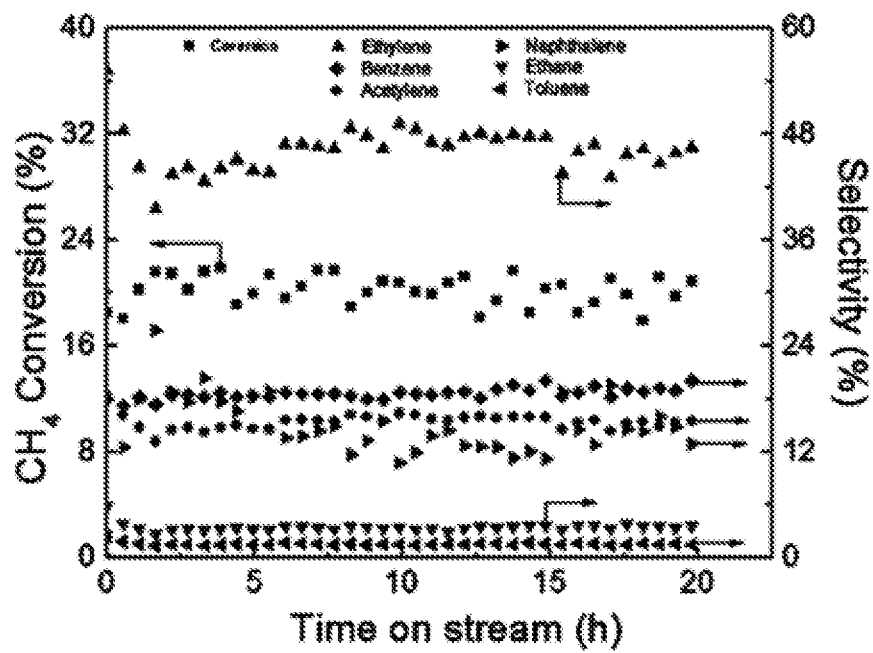
FIG. 16
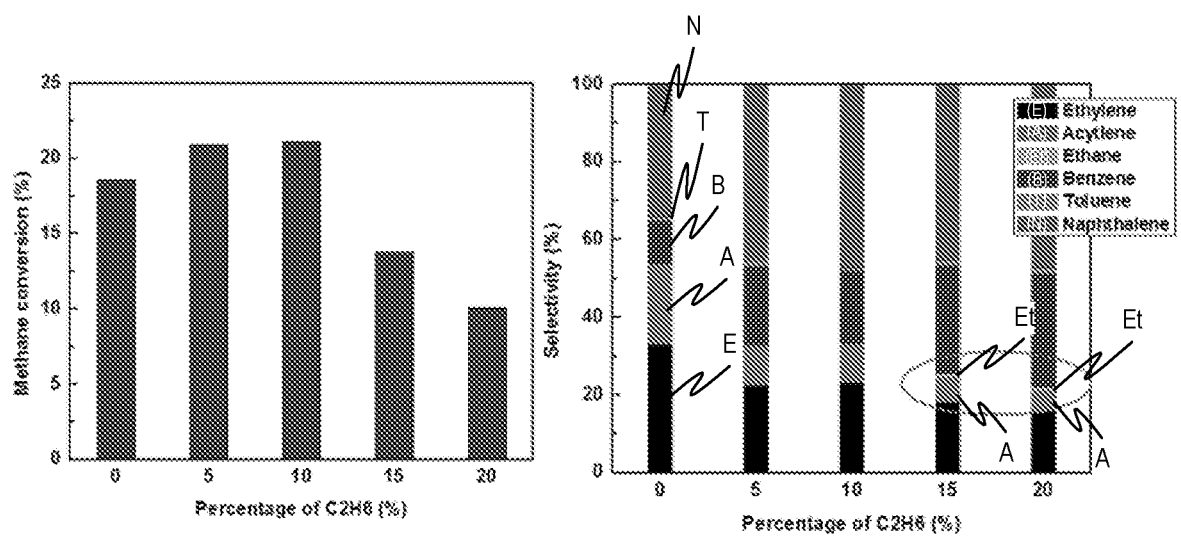
FIG. 17A
FIG. 17B

SYSTEMS, METHODS, AND DEVICES FOR DIRECT CONVERSION OF METHANE

CROSS-REFERENCE TO RELATED APPLICATIONS

The present application claims the benefit of U.S. Provisional Application No. 62/238,474, filed Oct. 7, 2015 and U.S. Provisional Application No. 62/300,338, filed Feb. 26, 2016, both of which are hereby incorporated by reference herein in their entireties.

STATEMENT REGARDING FEDERALLY SPONSORED RESEARCH

This invention was made with government support under CBET 1264599 and CBET 1351384 awarded by National Science Foundation (NSF). The government has certain rights in the invention.

FIELD

The present disclosure relates generally to methane conversion, and more particularly, to reactors that directly convert methane to hydrogen ($H_2$), $C_2$ hydrocarbons and/or aromatics.

BACKGROUND

Methane ($CH_4$) is an abundant natural resource as the main constituent of natural gas and oil-associated gases. However, methane has a configuration that renders it thermodynamically stable thereby inhibiting efficient utilization, e.g., as a fuel. Conversion of methane to other valued-added materials, such as $C_2$ hydrocarbons (e.g., acetylene, ethylene, ethane) and higher hydrocarbons such as aromatics (e.g., benzene and naphthalene), which combined are referred to as $C_{2+}$ hydrocarbons, is thus necessary.

Conversion of methane to other components can occur via indirect conversion or direct conversion (i.e., oxidative coupling of $CH_4$ to $C_{2+}$ hydrocarbons or non-oxidative direct methane conversion (NDMC)). In indirect conversion, methane is first converted to an intermediary (e.g., syngas ($CO+H_2$)) using partial oxidation or by reforming. The value-added materials can then be formed by converting from the intermediary, for example, using Fischer-Tropsch synthesis of higher hydrocarbons. In oxidative coupling of $CH_4$, the more reactive nature of $C_{2+}$ products as compared to methane leads to undesired sequential oxidation of $C_{2+}$ to thermodynamically favored $CO_x$ (i.e., either CO or $CO_2$). Such indirect or oxidative coupling conversions are, however, susceptible to high production and environmental costs, in particular large carbon dioxide emissions.

In contrast, NDMC forms $C_{2+}$ hydrocarbons and $H_2$ while avoiding the intermediate energy intensive steps required by the indirect or oxidative coupling conversion approaches. However, existing NDMC efforts suffer from kinetic and thermodynamic constraints that yield low $CH_4$ conversion at practical reaction conditions.

SUMMARY

Embodiments of the disclosed subject matter provide non-oxidative direct methane conversion (NDMC) to value-added products, such as $H_2$, $C_2$ hydrocarbons and aromatics, while avoiding the pitfalls and deficiencies of previous conversion methods. The NDMC can take place within a reactor heated to an elevated temperature. The reactor can have a first volume, where a feed gas including methane is provided, separated from a second volume, where a sweep gas is provided, by an $H_2$-permeable wall. The $H_2$-permeable wall includes a dense mixed ionic-electronic permeable thin film membrane supported on a porous wall and transports $H_2$ generated in the first volume by the conversion reaction to the second volume for removal by (or reaction with) the sweep gas. The removal of $H_2$ from the first volume can lead to significant increase in the amount of methane converted (up to 40%), while maintaining product selectivity for $C_2$ hydrocarbons and aromatics. A catalyst can be provided in or adjacent to the first volume for catalyzing the conversion of methane to the valued-added products. For example, the catalyst can be an $Fe(c)SiO_2$ or metal/zeolite (e.g., Mo/ZSM5) material. In certain configurations, the catalyst can be formed into a tube that communicates with the first volume to deliver a feed gas thereto. $CH_4$ conversion and/or product selectivity in the reactor can be manipulated by control of gas flow rates, reaction temperatures, and/or feed and sweep gas compositions.

In one or more embodiments, a method of converting methane comprises flowing methane in a first volume so as to contact a catalyst in a reactor while heating the reactor to an elevated temperature. The method can further include transporting hydrogen ($H_2$) from the first volume to a second volume in the reactor via a membrane supported within the reactor, and removing products from the first volume. The products can comprise $C_{2+}$ hydrocarbons and/or aromatics.

In one or more embodiments, a methane conversion device comprises a reactor, a membrane, and a catalyst. The reactor can have first and second gas volumes separated by the membrane. The catalyst can be disposed to interact with gas of the first gas volume. The membrane can be constructed to transport $H_2$ between the first and second gas volumes.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 16 is a graph of methane conversion percentage (left axis) and conversion product selectivity (right axis) over time for an $Fe(c)SiO_2$ catalyst in a packed-bed membrane reactor, at reaction temperature of 1303K and a feed gas space velocity of 3200 mL-$g^{-1}$-$h^{-1}$.

FIG. 17A is a graph of methane conversion percentage versus $C_2H_6$ feed fraction for an $Fe(c)SiO_2$ catalyst in a fixed-bed reactor, at a reaction temperature of 1303K and feed gas flow rates of 20 mL/min.

FIG. 17B is a graph of conversion product selectivity versus $C_2H_6$ feed fraction for an $Fe(c)SiO_2$ catalyst in a fixed-bed reactor, at a reaction temperature of 1303K and feed gas flow rates of 20 mL/min.

DETAILED DESCRIPTION

Non-oxidative direct methane conversion (NDMC) to value-added products, such as $H_2$, $C_2$ hydrocarbons and aromatics, can be achieved by providing methane to and heating a reactor according to one or more embodiments of the disclosed subject matter. In its simplest form, the reactor can have a first volume where a feed gas, including methane, is provided, and a second volume where a sweep gas is provided. The first volume can be separated from the second volume by a porous wall. The conversion of methane to the value-added products can occur within the first volume, and the products and unconverted methane removed via an outlet of the first volume.

In one or more embodiments, the wall separating the first and second volumes is constructed to transport $H_2$ therethrough at elevated temperatures (e.g., >873K). The removal of $H_2$ from first volume (where the methane conversion reaction is taking place) can improve the conversion efficiency for the methane (e.g., up to 40%). Thus, in some embodiments, the wall separating the first and second volumes includes a dense, mixed ionic-electronic permeable thin film membrane and a porous support.

Figure 1A:
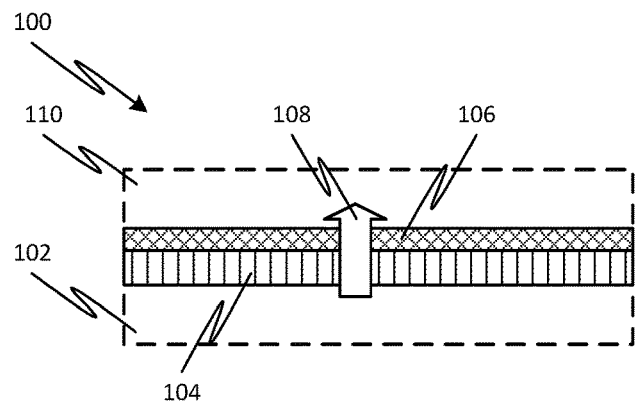
FIG. 1A illustrates aspects of a methane conversion device, according to one or more embodiments of the disclosed subject matter.

An exemplary structure 100 is shown in FIG. 1A. A first gas volume 102 is separate from a second gas volume 110 by a porous support 104 and a permeable membrane 106 formed on a surface of the support 104. Although shown as formed on a surface of the support 104 adjacent to the second gas volume 110, it is also possible to have the membrane 106 formed on the surface of the support 104 adjacent to the first gas volume 102, or to have membranes 106 formed on both surfaces of support 104, according to one or more contemplated embodiments. The membrane 106 is constructed to allow protonic/electronic transport 108 between the first and second gas volumes, such that $H_2$ produced during methane conversion can be removed from the first gas volume 102 to the second gas volume 110. Note that the $H_2$ transport 108 through the membrane is view bulk diffusion, i.e., ion transport without application of an external electric field.

For example, the permeable gas membrane can be a ceramic or ceramic composite, such as a perovskite-type oxide conductor. The porous support may be formed of a same or different material than the permeable gas membrane. For example, the porous support can be a ceramic or ceramic composite, such as a perovskite-type material. In embodiments, the material of the permeable gas membrane and the porous support are selected so as to have substantially the same coefficients of thermal expansion. The permeable gas membrane can be formed on the porous support and have a thickness of 50 μm or less, for example, 30 μm or less, or even 20 μm or less. The porous support, in contrast, could have a thickness on the order of hundreds of microns, for example, 1 mm.

For example, the perovskite-type oxide conductor for the membrane can have a formula of $M'Ce_{1-x-y}Zr_xM''_yO_{3-\delta}$, where M' is Sr or Ba, M'' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb, x is between 0.1 and 0.2, inclusive, y is between 0.1 and 0.3, inclusive. For example, an exemplary membrane can be formed of $SrCe_{0.7}Zr_{0.2}Eu_{0.1}O_{3-\delta}$ ceramic. The porous support can be formed of a material having a formula of $M'Ce_{1-x}Zr_xO_{3-\delta}$, where M' is Sr or Ba, and x is between 0.1 and 0.3, inclusive. For example, an exemplary support can be formed of $SrCe_{0.8}Zr_{0.2}O_3$.

Other suitable materials for the permeable membrane and/or porous support can be found in, for example, U.S. Pat. No. 6,296,687 entitled "Hydrogen Permeation Through Mixed Protonic-Electronic Conducting Materials," U.S. Pat. No. 6,235,417 entitled "Two-Phase Hydrogen Permeation Membrane," and U.S. Pat. No. 8,845,768 entitled "Proton Conducting Membranes for Hydrogen Production and Separation," all of which are hereby incorporated by reference herein, in their entireties. For example, the perovskite-type oxide can be represented by the general formula $ABO_3$, where A is at least one element selected from the group consisting of Ba, Ca, Mg and Sr; B is $Ce_{1-x}M_x$ or $Zr_{1-x}M_x$; M is a multivalent dopant metal, for example, an element selected from the group consisting of Y, Yb, In, Gd, Nd, Eu, Sm and Tb; and x is greater than 0 and less than 1, for example, between 0.05 and 0.40, inclusive.

Figure 1B:
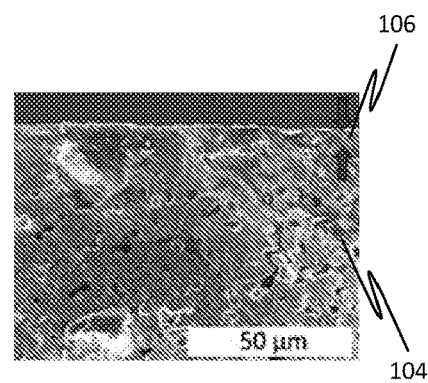
FIG. 1B is a cross-sectional image of a fabricated $H_2$-permeable membrane and porous support.

The membrane can be formed on a surface of the support to a thickness of between 1 μm and 50 μm. For example, FIG. 1B shows a cross-sectional view of a fabricated permeable membrane 106 (e.g., $SrCe_{0.7}Zr_{0.2}Eu_{0.1}O_{3-\delta}$) formed on a porous support 104 (e.g., $SrCe_{0.8}Zr_{0.2}O_{3-\delta}$). The support can be coated on one or both of its surfaces (although only one is shown) with the membrane material and sintered to form the structure illustrated in FIG. 1B. The thickness of the membrane 106 is approximately 20 μm with an active surface area of 12 $cm^2$. In an embodiment, the support 104 can be a circular tube with a 1 mm-thick wall and a diameter of 6 mm. Alternatively, the support can be formed as a plate, rectangular tube, or any other geometry.

Figure 2:
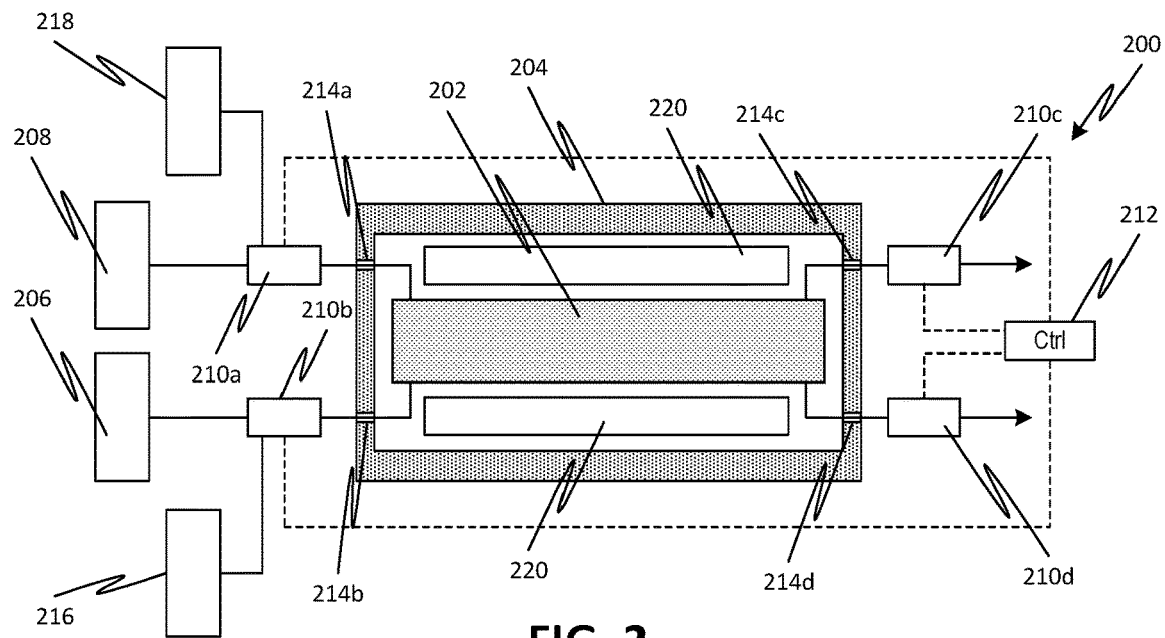
FIG. 2 illustrates aspects of a methane conversion system with reactor, according to one or more embodiments of the disclosed subject matter.

Referring to FIG. 2, a generalized system 200 for direct conversion of methane is illustrated. The system 200 can include a reactor 202, which can include (but not illustrated) first and second gas volumes separated by a porous wall and membrane, for example, as illustrated in FIG. 1A. The reactor 202 can be contained within a furnace 204 and heated by a heater 220 to the desired reaction temperature (e.g., above 1000K). The heater 220 and furnace 204 together may comprise a heating module. Although a specific configuration for the heating module is illustrated in FIG. 2, alternative heating methodologies and configurations are also possible according to one or more contemplated embodiments. For example, instead of or in supplement to heater 220, heat within furnace 204 can be generated via an exothermic reaction between gas constituents in the first and/or second gas volumes, such as between a sweep gas of air or steam and transported $H_2$ gas.

Methane can be provided from a primary feed gas source 206 to the reactor 202 via a respective inlet line that passes through a wall of the furnace 204, e.g., via respective heat seal 214b. In certain embodiments, the gas provided to the first gas volume of the reactor consists essentially of methane, i.e., minor concentrations (e.g., <20%) of other gases (such as, but not limited to, a tracer or inert gas) may be included but do not otherwise affect the reaction. In other embodiments, a secondary feed gas from one or more secondary feed gas sources 216 can be provided to the first gas volume to tune the conversion efficiency and/or selection of products, as described in further detail below. The resulting products and/or any remaining unconverted methane can be removed from the first volume of the reactor 202 via a respective outlet line that passes through a wall of the furnace 204, e.g., via respective heat seal 214d. The products can be separated from the methane for subsequent use or storage, while the unconverted methane may be recirculated back to source 206 or the first gas volume of the reactor 202 for conversion.

At a same time as the feed gas flow in the first gas volume of the reactor 202, a sweep gas flow can be provided in the second gas volume of the reactor 202. A primary sweep gas is provided from one or more primary sweep gas sources 208 to the reactor 202 via a respective inlet line that passes through a wall of the furnace 204, e.g., via respective heat seal 214a. For example, the sweep gas is helium (He) or another noble gas, so as not to react with any transported $H_2$ from the first volume to the second volume. In some embodiments, a secondary sweep gas of $H_2$ can be provided from secondary sweep gas source 218 can be provided to the second gas volume to modulate the transport of $H_2$ between the first and second volumes, thereby tuning the conversion efficiency and/or product selection.

In some embodiments, the primary sweep gas is specifically selected to react with the transported $H_2$. For example, the sweep gas can be air or steam and can react with the transported $H_2$ to form water. In another example, the sweep gas can be $N_2$ and can react with the transported $H_2$ to form $NH_3$ (ammonia). In still another example, the sweep gas can be $CO_2$ or CO and can react with the transported $H_2$ to form syngas, methanol, di-methyl ether, higher alcohols, and/or other hydrocarbons. In such embodiments, a secondary catalyst may be provided adjacent to or within the second gas volume to catalyze the reaction between the sweep gas and the $H_2$. For example, a nickel (Ni) catalyst or other oxidation catalyst may be used on the sweep side, such as in the annular space between the porous support and an outer housing, or on a surface of either. Alternatively or additionally, the secondary catalyst can comprise Ni, Cu, Zn, or Fe supported on a metal oxide support, such as, but not limited to, $SiO_2$, $Al_2O_3$, $ZrO_2$, and $CeO_2$.

The resulting products, unconverted sweep gas, and/or transported $H_2$ can be removed from the second volume of the reactor 202 via a respective outlet line that passes through a wall of the furnace 204, e.g., via a respective heat seal 214c. The products and/or $H_2$ can be separated from the sweep gas for subsequent use or storage, while the unconverted sweep gas may be recirculated back to source 208 or the second gas volume of the reactor 202 for repeated use.

The system 200 can include a controller 212 which regulates operation thereof and can modify flow rates, feed gas composition, sweep gas composition, and/or temperature to regulate methane conversion efficiency and/or product selectivity, as described in more detail below. Each of the input and output lines can include a respective gas flow control and sensing module 210a-210d, which may include, for example, valves, temperature sensors, temperature controllers, pumps, and/or other devices to monitor and/or control the variables of gas flow rates, reaction temperatures, and/or feed and sweep gas compositions to optimize or otherwise control methane conversion product formation, as described herein.

In some embodiments, the reactor 202 can be configured as a tubular reactor, with an inner tube defining the first gas volume and an annular space between the inner tube and an outer tube serving as the second gas volume. A wall of the inner tube can be formed with the permeable membrane thereon, such that the reactor can be considered a tubular membrane reactor. In addition, a catalyst can be provided in or adjacent to the first gas volume so as to catalyze the desired methane conversion, such that the reactor can be considered a packed-bed tubular membrane reactor.

Figure 3A:
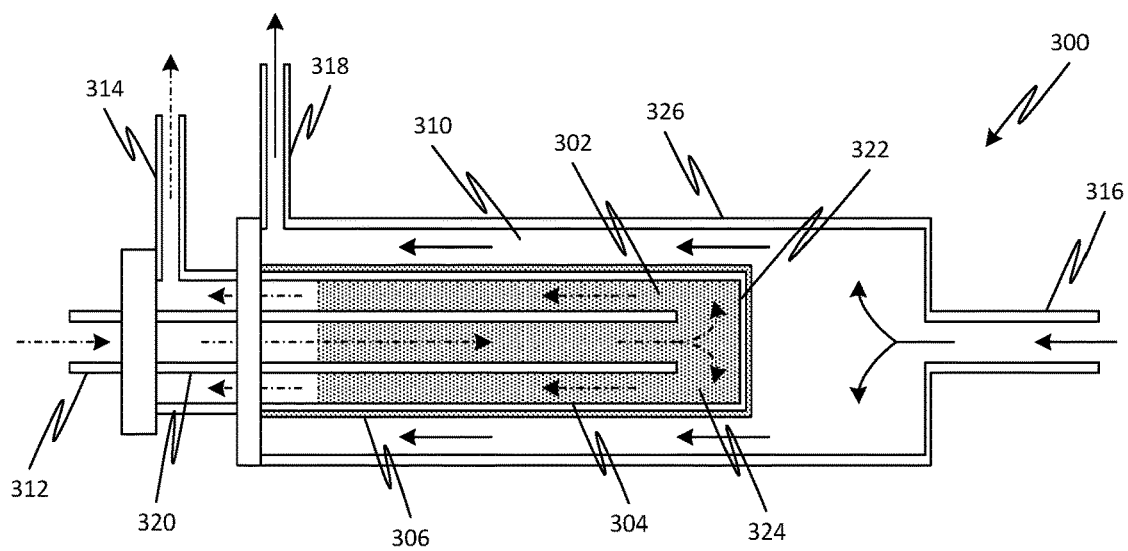
FIG. 3A shows a cross-sectional view of an exemplary membrane reactor that can be used in the setup of FIG. 2, according to one or more embodiments of the disclosed subject matter.

An exemplary configuration of such a packed-bed tubular membrane reactor 300 is illustrated schematically in FIG. 3A. The reactor 300 can have a first gas volume 302 formed by the interior volume of a porous support tube 304. A permeable membrane 306 can be provided on a surface of the support tube 304, for example, on the radially outer surfaces of the support tube 304. Feed gas can be provided to the first gas volume 302 via gas inlet 312, where an inlet tube 320 disposed within the porous support tube 304 conveys the feed gas down to the first gas volume 302 into contact with a catalyst 324.

As illustrated in FIG. 3A, the porous support tube 304 can be provided with an end cap portion 322, which may be integral with the support tube 304 or a separate piece adhered to the support tube 304. In some embodiments, the end cap portion 322 may also be provided with a membrane 306 thereon. The porous support tube 304 is thus closed at one end and opened at the other. The feed gas is thus redirected by the end cap 322 back toward the inlet along the first gas volume 302 to a respective outlet 314. Alternatively, the porous support tube 304 can be open at both ends, in which case the outlet 314 can be disposed at end of the reactor 300 opposite from the inlet 312.

The reactor 300 can also have a second gas volume 310 formed by the annular space between the porous support tube 304 and an outer enclosure 326, e.g., a quart tube. Sweep gas can be provided to the second gas volume 310 via gas inlet 316 and exits the second gas volume 310 via a respective outlet 318.

A catalyst 324 can be provided in or adjacent to the first volume 302 for catalyzing the conversion of methane to the valued-added products. For example, the catalyst can be an $Fe(c)SiO_2$ or Mo/ZSM5 material, preferably $Fe(c)SiO_2$, where (c) denotes confinement and represents a catalyst characterized by the lattice-confined single iron sites embedded within a silica matrix. Although shown as extending to within inlet tube 320 and the first gas volume 302, it is also possible that the catalyst 324 can be disposed in other locations according to one or more contemplated embodiments. For example, the catalyst 324 can be disposed outside the inlet tube 320, for example, between the end cap 322 and an outlet end of the inlet tube 320 and/or in the annular space between the inlet tube 320 and the radially inner wall of the porous support 304.

Figure 3B:
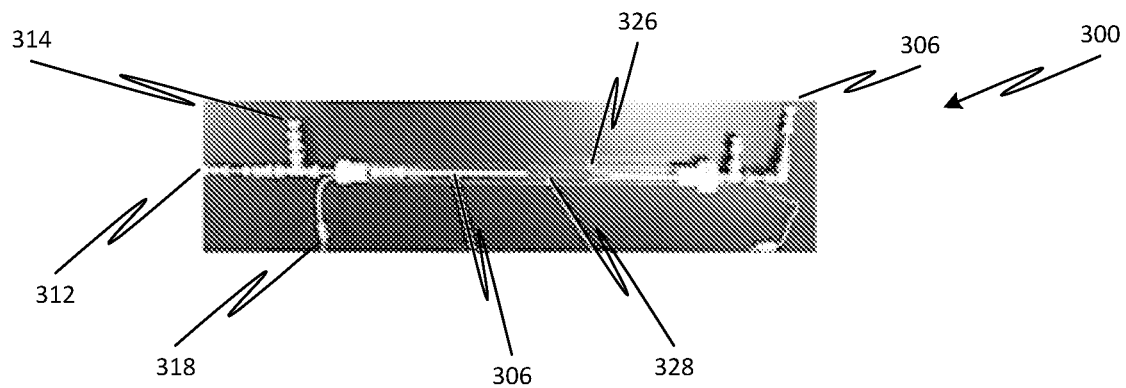
FIG. 3B is an image illustrating the setup of a fabricated membrane reactor.

FIG. 3B shows an image of a test setup employing the packed-bed tubular membrane reactor similar to FIG. 3A. The test set-up shown in FIG. 3B was used for NDMC reactions. The $CH_4$ stream was introduced at inlet 312 to the first gas volume (i.e., from the left section of the reactor unit 300). After contact with the catalyst, the effluent gases (reactants+products) exit at outlet 314 (i.e., from the left section of the reactor unit 300). The sweep gas (e.g., He) is passed through the annular area (i.e., second gas volume) of the tubular membrane reactor to carry permeated hydrogen from the reaction system via outlet 318 on an opposite side of the reactor 300 from inlet 306. A temperature sensor 328 can be disposed within the outer housing 326 to monitor reaction temperature and allow heating adjustment, if needed. The effluents of both the sweep side and the reaction side were analyzed by gas chromatography and mass spectrometry to determine the methane conversion and product selectivity.

Figure 3C:
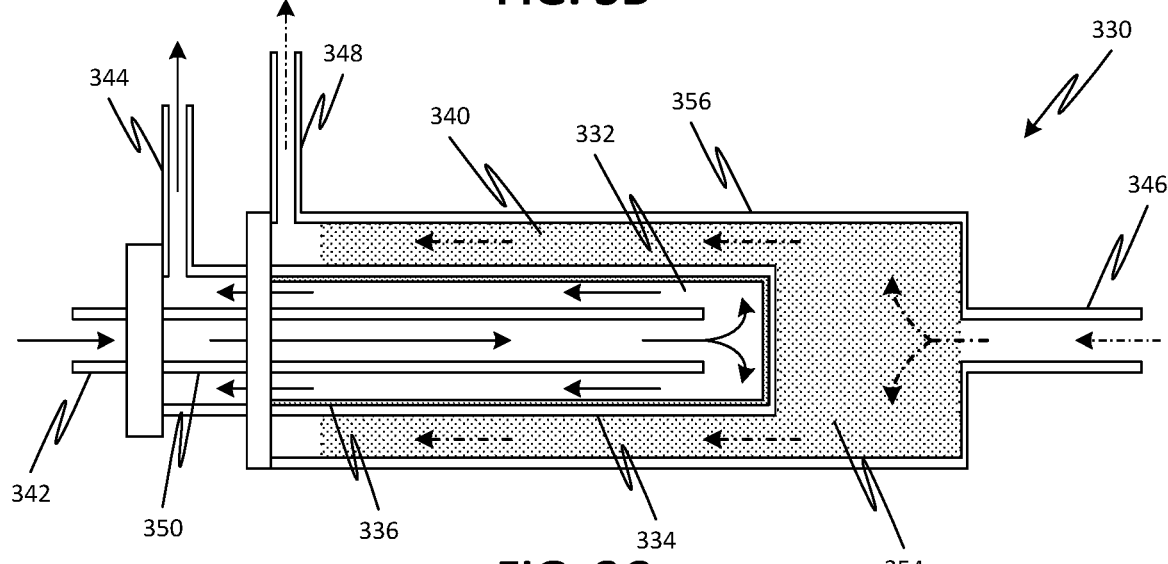
FIG. 3C shows a cross-sectional view of another exemplary membrane reactor that can be used in the setup of FIG. 2, according to one or more embodiments of the disclosed subject matter.

In an alternative configuration of the packed-bed tubular reactor, the sweep gas can be provided to the inner tube and the feed gas can be provided to the outer annular region. FIG. 3C illustrates such a reactor 330, which is similar to the reactor 300 of FIG. 3A but the feed/sweep inlets and outlets have been swapped, and the locations of the catalyst and membrane have been moved. Thus, feed gas is provided to the first gas volume 340 via gas inlet 346, where it comes into contact with catalyst 354. Although shown as substantially filling the first gas volume 340, it is also contemplated that catalyst 354 may dispose more or less volume than that illustrated in FIG. 3C. The first gas volume 340 may be formed between an inner wall of the outer enclosure 356 and an outer wall of the inner tube 334.

The second gas volume 332 of the reactor 330 is formed within the interior volume of the inner tube 334. Sweep gas can be provided to the second gas volume 332 via gas inlet 342, where an inlet tube 350 disposed within the support tube 334 conveys the sweep gas to the inner tube 334. As with the embodiment of FIG. 3A, the inner tube 334 can be closed at one end, as illustrated, or it may be opened at both ends.

The permeable membrane 336 is disposed on a surface of the porous inner support tube 334. But in contrast to the configuration of FIG. 3C, the membrane 336 is disposed on an inner surface (e.g., radially inner surface) of the support tube 334. In general, the membrane 336 may be disposed closer to the second gas volume 332 than the first gas volume 340, i.e., on a second-gas-volume side of the support tube 334.

As with the embodiment of FIG. 3A, the feed gas entering the first gas volume 356 interacts with catalyst 354 and undergoes a reaction at elevated temperatures that results in the production of $C_2$ hydrocarbons and aromatics, which are conveyed from the first gas volume via outlet 348, and $H_2$, which is transported via porous support 334 and permeable membrane 336 to the second gas volume 332. In the second gas volume 332, the $H_2$ potentially reacts with the sweep gas and is subsequently removed via outlet 344.

Figure 3D:
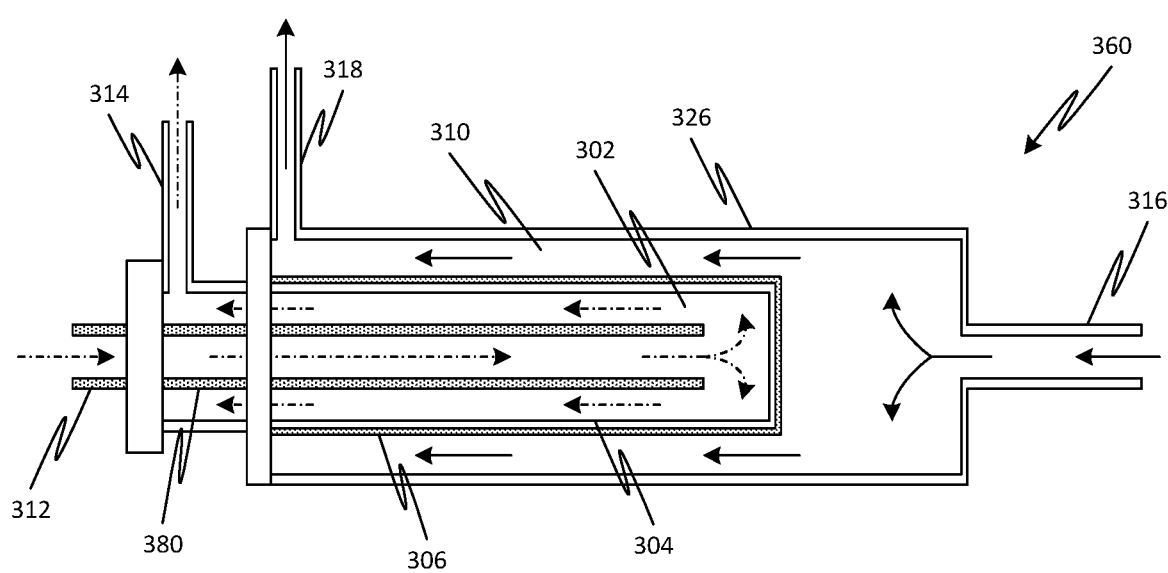
FIG. 3D shows a cross-sectional view of an exemplary membrane reactor with catalytic tube that can be used in the setup of FIG. 2, according to one or more embodiments of the disclosed subject matter.
Figure 3E:
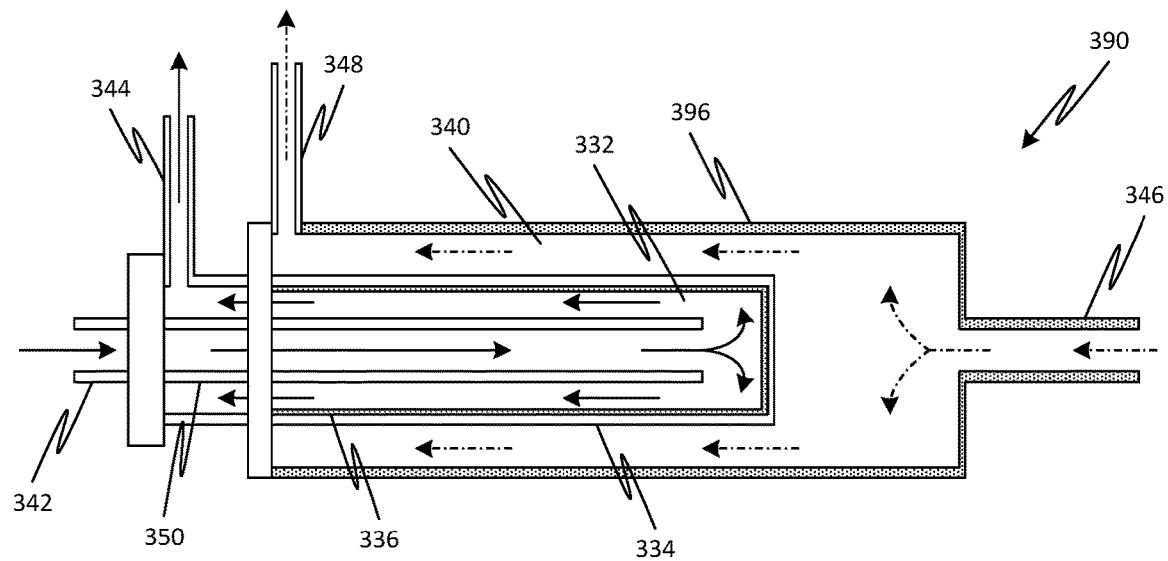
FIG. 3E shows a cross-sectional view of another exemplary membrane reactor with catalytic tube that can be used in the setup of FIG. 2, according to one or more embodiments of the disclosed subject matter.

Although FIGS. 3A and 3C discuss reactor configurations with a catalyst filling all or portion of the gas volume therein, embodiments of the disclosed subject matter are not limited thereto. Rather, it is also possible to incorporate the catalyst into one or more structures within the reactors, for example, surfaces or walls of the feed gas flow channels. For example, FIG. 3D shows an embodiment of a reactor 360 with such a variation. In particular, reactor 360 is substantially identical to the reactor 300 of FIG. 3A, but the inlet tube 320 has been replaced with a catalytic tube 380. Feed stock provided to the first gas volume 302 thus contacts and interacts with the catalyst within tube 380 as it travels from inlet 312, down to capped end 322, and then back to outlet 314. In another example, FIG. 3E shows an embodiment of a reactor 390, which is substantially identical to the reactor 330 of FIG. 3C except for catalytic enclosure 396. Thus, feed stock provided to the first gas volume 340 contacts and interacts with the catalyst within the enclosure 396 as it travels from inlet 346 to outlet 348. For example, the catalyst forming the tube 380 or enclosure 396 can be an $Fe(c)SiO_2$ material.

Figure 3F:
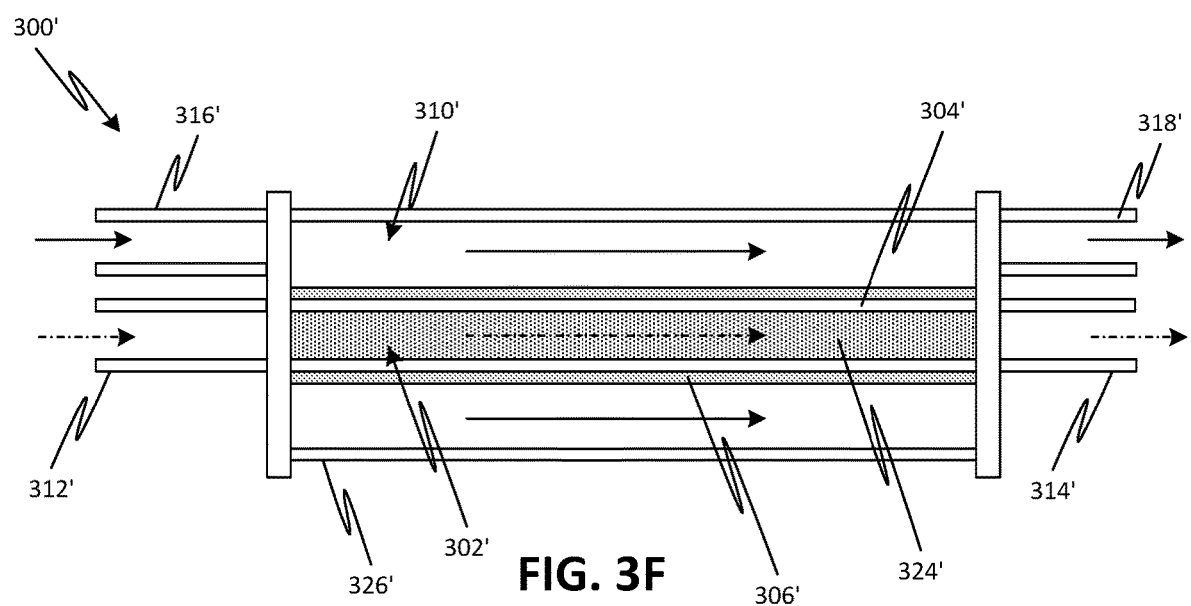
FIG. 3F shows a cross-sectional view of another exemplary membrane reactor with open tube configuration that can be used in the setup of FIG. 2, according to one or more embodiments of the disclosed subject matter.

Although the inner support tube has been illustrated with an end cap in FIGS. 3A-3E, embodiments of the disclosed subject matter are not limited thereto. Rather, other flow path configurations are also possible according to one or more contemplated embodiments. For example, FIG. 3F shows a reactor 300' where a feed gas flows from an inlet 312' at one end of support tube 304' to an outlet 314' at an opposite end of the support tube 304' (i.e., without end cap 322 of FIG. 3A). Similarly, the sweep gas can be introduced to the second volume 310' defined between the support tube 304' and an outer enclosure 326' via inlet 316'. Contents of the second volume 310' can be removed via outlet 318' on an opposite end of the enclosure 326'. The inlet 312' and inlet 316' may be on a same side, as illustrated in FIG. 3F, or on opposite sides, such that the direction of the feed gas flow is opposite to a direction of the sweep gas flow. Similar to FIG. 3A, the first gas volume 302' can have a catalyst 324' therein, and a membrane 306' may be formed on a surface of the support 304' adjacent to the second gas volume 310'. Alternative configurations for the reactor 300' are also possible, for example, similar to FIG. 3C (where flow paths for the sweep and feed gases are swapped, and the membrane and catalyst are relocated accordingly) and/or FIGS. 3D-3E (where the catalyst is formed as part of the structure defining the first gas volume or as part of a structure conveying feed gas to the first gas volume).

Although inlet tube 380 and enclosure 396 are illustrated as being completely formed of the catalytic material in FIGS. 3D-3F, embodiments of the disclosed subject matter are not limited thereto. Rather, other configurations are also possible according to one or more contemplated embodiments. For example, the catalytic material may be integrated in a portion of the inlet tube 380 or enclosure 396, such as only along an axial distance where it overlaps with the porous support tube 304/334. Alternatively or additionally, the catalytic material may be integrated onto a surface of the inlet tube 380 or enclosure 396 that faces the respective first volume, thereby allowing the remainder of the tube 380 or enclosure 396 to be formed of another material. Alternatively or additionally, the catalyst may be integrated with the end cap 322 such that flow in first volume 302 from inlet tube 380 (FIG. 3D) or in first volume 340 from inlet 346 (FIG. 3E) contacts it. In such a configuration, the porous support 304/334 may be formed of a different material than the end cap 322.

Figure 4:
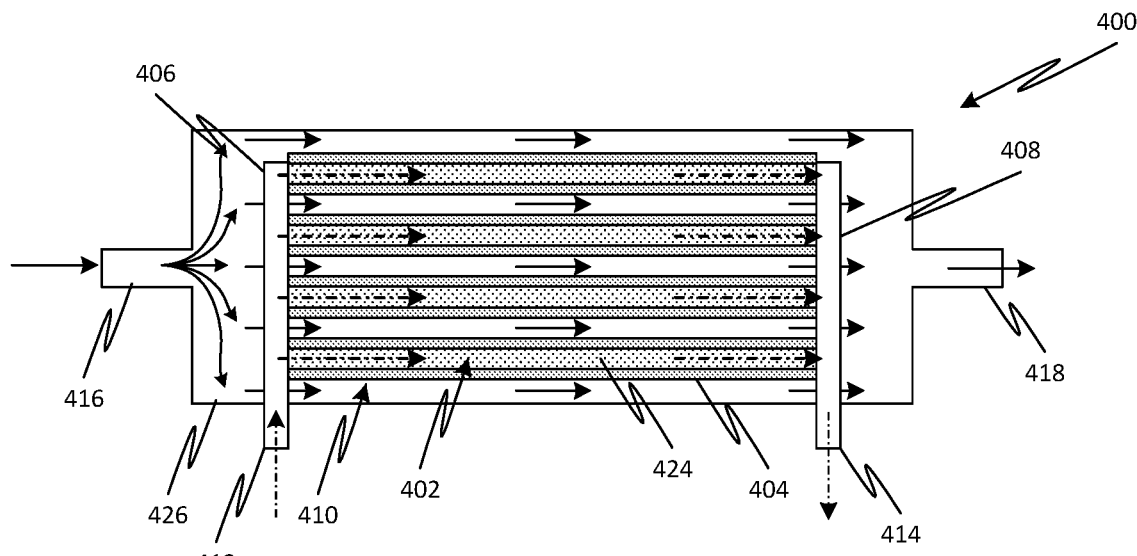
FIG. 4 shows a cross-sectional view of an exemplary arrayed membrane reactor that can be used in the setup of FIG. 2, according to one or more embodiments of the disclosed subject matter.

Although only a single reactor is illustrated in FIGS. 3A-3F, embodiments of the disclosed subject matter are not limited thereto. Indeed, large scale embodiments of the disclosed subject matter may include an array of reactors, or an array of reactor portions, to allow simultaneous processing of a methane source. For example, FIG. 4 illustrates an exemplary configuration of an array setup 400, where multiple porous support tubes with membranes 404 define respective first gas volumes 402 within a larger housing 426. A shared second gas volume 410 can then be defined between the individual porous support tubes with membranes 404 and the larger housing 426. Each of the first gas volumes 402 can include a catalyst 424 packed therein.

Feed gases can be provided to the first gas volumes 402 via an inlet manifold 412, and the unreacted feed gas and products can be removed from the first gas volumes 402 via an outlet manifold 414. Sweep gases can be provided to the second gas volume 410 via inlet 416, and unreacted sweep gas, products, and/or transported $H_2$ can be removed from the second gas volume via outlet 418.

It should be readily apparent to one of ordinary skill in the art that the configuration of FIG. 4 can also be applied to the embodiments of FIGS. 3C-3F, for example, by appropriate alteration of feed/sweep flows, membrane location, catalyst location, and/or integration of the catalyst. Such configurations are within the scope of disclosed subject matter. Moreover, other configurations for scaling up the packed-bed tubular membrane reactor of FIGS. 3A-3F are also possible according to one or more contemplated embodiments.

Figure 5:
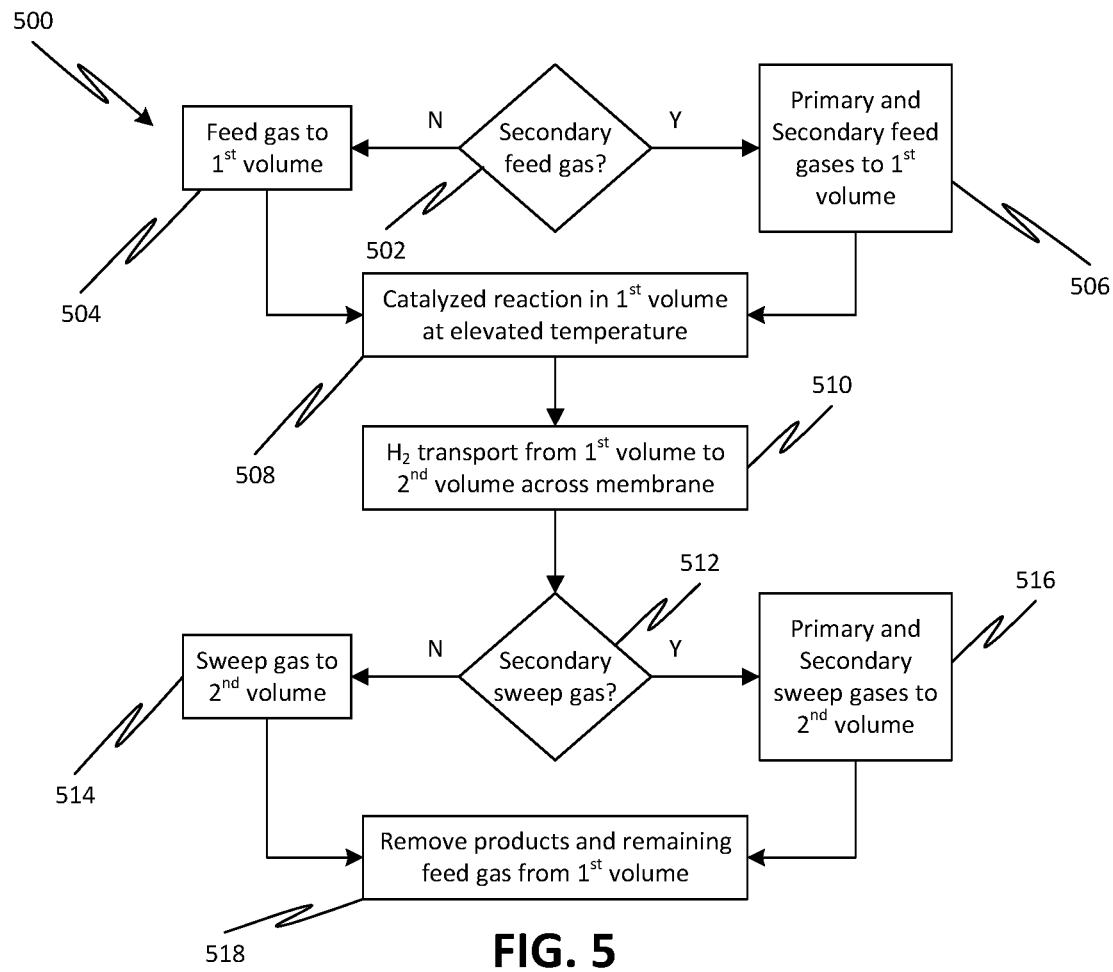
FIG. 5 is a process flow diagram for non-oxidative direct conversion of methane, according to one or more embodiments of the disclosed subject matter.

Referring to FIG. 5, a generalized process 500 for converting methane to value-added products using a membrane reactor is shown. The process 500 begins at 502 where it is determined if a secondary feed gas is desired. If yes, the process proceeds to 506 where primary and secondary feed gases are supplied to the first volume. As noted above, the primary feed gas consists essentially of methane, i.e., it can have minor concentrations of tracer or inert gases that do not otherwise affect the conversion reactions. The secondary feed gas can include, for example, $H_2$, $C_2H_2$, $C_2H_4$, $C_2H_6$, or any other hydrocarbon gas, such as, but not limited to, propane, butane, heptane, benzene, toluene, xylene, or an impurity hydrocarbon from shale gas. The secondary feed gas can be used to tune the methane conversion efficiency and/or selection of products, as described in further detail herein. Otherwise the process proceeds from 502 to 504, where only the primary feed gas is supplied to the first volume.

The process then proceeds to 508 where the feed gases in the first volume interacts with the catalyst at an elevated temperature to convert the methane via the desired product reaction. For example, the reactor is heated to a temperature of at least 1000K. At 510, $H_2$ produced by the methane conversion is transported from the first volume to the second volume via the permeable membrane separating the two volumes.

At 512, it is determined if a secondary sweep gas is desired. If no, the process proceeds to 514 where only a primary sweep gas is supplied to the first volume. For example, the sweep gas can be helium (He) or another noble gas, so as not to react with any transported $H_2$ from the first volume to the second volume. In some embodiments, the primary sweep gas is specifically selected to react with the transported $H_2$. For example, the sweep gas can be air or steam and can react with the transported $H_2$ to form water. The heat from this exothermic reaction can be used to heat the reactor in 508. In another example, the sweep gas can be $CO_2$ or CO and can react with the transported $H_2$ to form syngas, methanol, di-methyl ether, higher alcohols, and/or other hydrocarbons. In still another example, the sweep gas can be $N_2$ and can react with the transported $H_2$ to form ammonia ($NH_3$).

If yes, the process proceeds to 516 where primary and secondary sweep gases are supplied to the second volume. As noted above, the secondary sweep gas can be $H_2$ and can be used to modulate the transport of $H_2$ between the first and second volumes, thereby tuning the conversion efficiency and/or product selection. The process then proceeds to 518 where the products and unreacted feed gas are removed from the first volume. The contents of the second volume, e.g., unreacted sweep gas, $H_2$, and/or reaction products (e.g., water, ammonia, or syngas), can also be removed from the second volume at 518. The removed gases can be analyzed, separated, and/or processed for subsequent use. For example, unreacted feed gas or sweep gases can be resupplied to their respective inlets of the reactor for reprocessing. Desired products, such as $C_2$ hydrocarbons, aromatics, $H_2$ gas, ammonia, and/or syngas, can be separated and stored.

Although illustrated as separate steps, it is contemplated that various steps may occur simultaneously or iteratively. For example, the determinations regarding secondary feed gas 502 and secondary sweep gas 512 can repetitively occur at the same time as the other steps to allow the conversion efficiency and/or product selection to be altered based on feedback of removed products or other analyses. Moreover, the product reactions 508, $H_2$ transport 510, sweep gas flows, and product removal 518 occur simultaneously despite being illustrated as sequential steps. Furthermore, certain steps illustrated as occurring after others may indeed occur before. For example, a sweep gas flow 514, 516 may be initiated before any feed gas flow 504, 506 begins.

In embodiments, the membrane reactor includes a porous support structure with a permeable membrane formed thereon and separating the first gas volume from the second gas volume. For example, the porous support structure can be formed of SrCeZrO while the permeable membrane can be formed of SrCeZrEuO. The powder can be prepared using the solid-state synthesis method, with $SrCO_3$, $CeO_2$, and $ZrO_2$ as starting materials. Other cations may also be included in the starting materials. For example, stoichiometric amounts of the starting materials can be mixed by a ball milling process, and sufficient amounts of ethanol (e.g., 200 proof) and milling media (e.g., yttria-stabilized zirconia) can be added to create homogeneity in the milling process. The resultant slurry can be ball milled for 24 hours, followed by drying, grinding into a fine powder, and then calcination at 1573 k for 10 hours. The as-obtained material was $SrCe_{0.8}Zr_{0.2}O_3$ perovskite ceramic.

As noted above, the porous support can be formed into a tubular structure. To form such a structure, the $SrCe_{0.8}Zr_{0.2}O_3$ powder can be made into a slurry for tape casting by mixing $SrCe_{0.8}Zr_{0.2}O_3$ powder and dispersant (e.g., Menhaden fish oil) in ethanol. The mixture can then be ball milled for 24 hours. A binder (e.g., polyvinyl butyral) and pasticizer (e.g., benzyl butyl phthalate) can be added to the mixture, and continued to ball mill for 48 hours. Lastly, a pore former (e.g., poly methyl methacrylate with particle size of 5 µm) can be added, and the ball milling continued for an additional 24 hours.

The final slurry can then be formed into the desired tubular shape, for example, via tape casting. For example, the tape can be rolled using a stainless steel tube, and then capped with a circular piece of the tape. The final tubular support can be pre-sintered at 1423K for 4 hours to form the one-end capped $SrCe_{0.8}Zr_{0.2}O_3$ porous tubular support.

Figure 6:
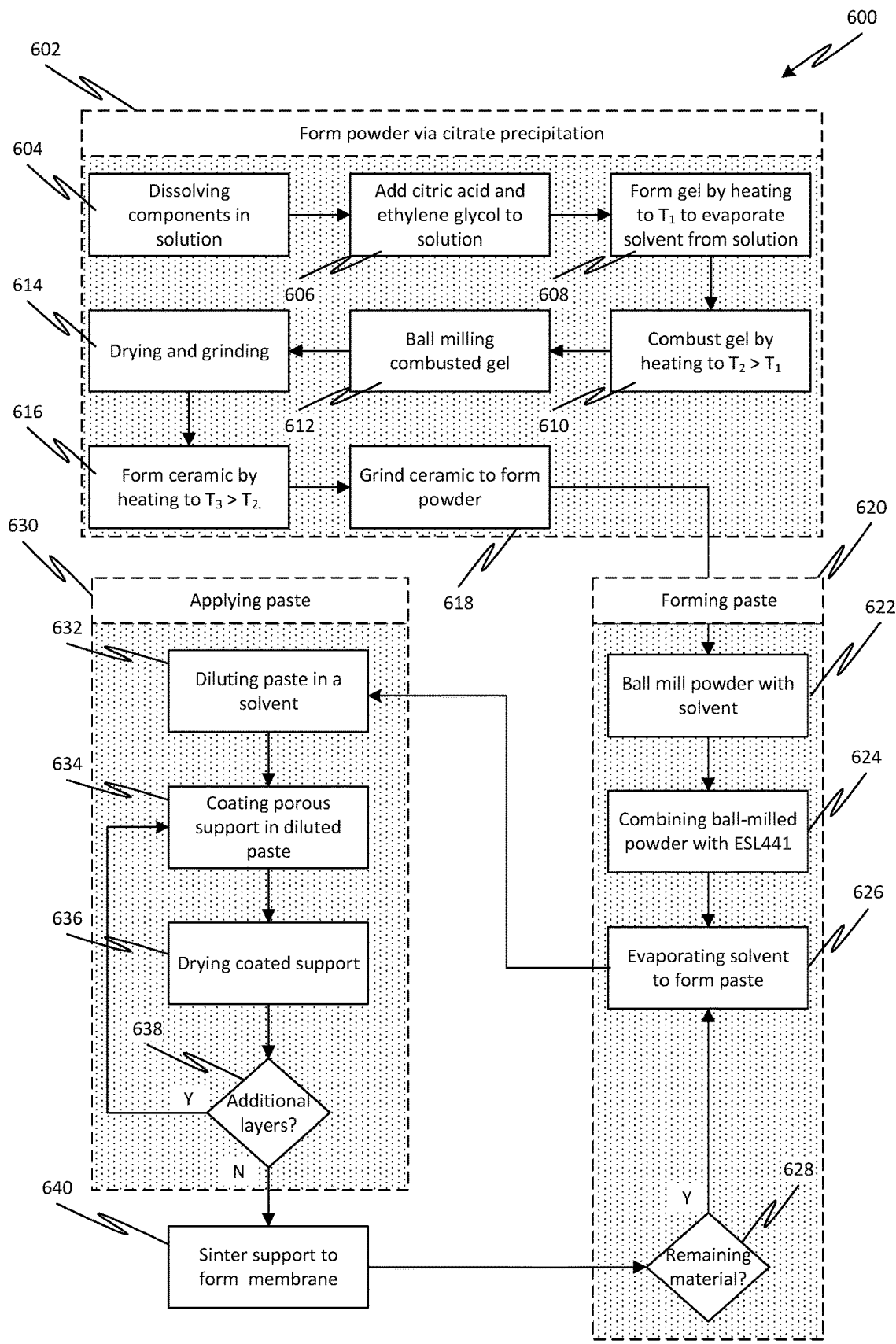
FIG. 6 is a process flow diagram for fabricating a permeable membrane, according to one or more embodiments of the disclosed subject matter.

Referring to FIG. 6, a generalized process 600 for forming a permeable membrane on the porous support is shown. The process 600 begins generally at 602 where a powder for the membrane is formed via citrate precipitation. At 604, stoichiometric amounts of $Ce(NO_3)_3 \cdot 6H_2O$, $Sr(NO_3)$, $ZrO(NO_3)_2 \cdot H_2O$, and $Eu(NO_3)_3 \cdot 6H_2O$ are dissolved in de-ionized water. At 606, citric acid and ethylene glycol are added to the solution. The molar ratio of the total metal nitrates to citric acid and ethylene glycol can be, for example, 1:2:2, in order to prevent the formation of secondary phases, and decrease the calcination temperature.

At 608, the solution can be heated to a first temperature (e.g., 393K), and maintained at that temperature in order to evaporate the water under constant stirring. Once all the water evaporates, a gel is formed. The process proceeds to 610 where the temperature is raised to a higher second temperature (e.g., 673K) in order to auto-ignite the combustion of the gel. Once the gel is combusted, the process proceeds to 612 where the resultant material can be ball milled for 24 hours in ethanol, followed by drying and grinding into fine powder at 614, and then calcination at a still higher third temperature (e.g., 1473K) for 10 hours at 616. The as-obtained material was $SrCe_{0.7}Zr_{0.2}Eu_{0.1}O_{3-\delta}$ perovskite ceramic, which can be formed into a powder by grinding the ceramic at 618, thereby concluding general process 602. As compared to the solid state synthesis method employed in forming the porous support, the citrate precipitation method 602 can yield more uniform mixing of the starting materials and thereby smaller particle sizes for the $SrCe_{0.7}Zr_{0.2}Eu_{0.1}O_{3-\delta}$ material.

The process 600 then proceeds from 602 to general process 620 where a paste is formed from the powder in order to prepare the $SrCe_{0.7}Zr_{0.2}Eu_{0.1}O_{3-\delta}$ slurry for colloidal coating. Note that the formation of the paste allows the membrane slurry to be stored and used directly without further milling. At 622, $SrCe_{0.7}Zr_{0.2}Eu_{0.1}O_3$ powder can be ball milled with a solvent (e.g., ethanol) for 24 hours. At 624, a commercial system, ESL441 (ESL ElectroScience), can be added to the mixture. ESL441 is an ester alcohol-based system with binder and plasticizer. At 626, the solvent can be evaporated from the mixture from 624 (or remaining material from 628) to form the paste, thereby concluding general process 620. For example, a planetary centrifugal mixer can be used to mix and evaporate all the ethanol until the remaining material is a paste consisting essentially of the ceramic powder and the ESL441 system.

The process 600 then proceeds from 620 to general process 630 where the paste is applied to the support in a colloidal coating process. At 632, the paste is diluted with a solvent (e.g., ethanol) to form a membrane slurry. Proceeding to 634, the pre-sintered tubular membrane support can then be coated (e.g., dip coating) with the membrane slurry. At 636, the coated support is then dried. Because thin membranes may shrink and break during subsequent sintering, repeated coatings of the membrane material may be desired to increase the final membrane thickness. If it is determined that additional coatings are needed at 638, the process returns to 634 for repetition until a desired thickness (e.g., 3 coatings to achieve a thickness of ~20 µm) is achieved. Otherwise, the general process 630 concludes and the process 600 proceeds to 640, where the coated support is sintered at 1793K for 6 hours. After the colloidal coating process 630, the paste can be recovered by re-evaporating the solvent, e.g., via the planetary centrifugal mixer at 626.

The procedure for synthesis of $SrCe_{0.7}Zr_{0.2}Eu_{0.1}O_{3-\delta}$ particles via the solid state method is listed below. For example, 5.53 g of strontium carbonate, 4.51 g of cerium oxide, 0.92 g of zirconium oxide, and 1.67 g of europium nitrate were used as starting materials to make 10 g of $SrCe_{0.7}Zr_{0.2}Eu_{0.1}O_{3-\delta}$ particles. After the required amounts of starting materials were measured out, they were mixed by a ball milling process. Sufficient amounts of ethanol and the milling media (e.g., yttria-stabilized zirconia) were added to help create homogeneity in the mixture. The resultant slurry was ball milled for 24 hours, followed by drying, grinding into fine powder, and then calcination at 1573K for 10 hours. The as-obtained $SrCe_{0.7}Zr_{0.2}Eu_{0.1}O_{3-\delta}$ perovskite ceramic material was then ground, and ball milled for an extra of 48 hours in order to reduce the particle size and increase homogeneity in particle size distribution. However, as noted above, the citrate precipitation method of FIG. 6 may result in a permeable membrane with superior structural integrity.

Prior to the usage of the $H_2$ permeable membrane reactor for NDMC over a catalyst, the membrane reactor underwent leakage and $H_2$ permeation tests. In particular, the tubular membrane reactor of FIG. 3B was used for these experiments. The feed side (e.g., radially inside of the membrane) was exposed to $H_2$ diluted to the tested concentration using Ar tracer. The total flow rate of the feed gas (mixture of $H_2$ and Ar) was set at 20 mL·min$^{-1}$. The sweep side (radially outside of the membrane) was exposed to He at 20 mL·min$^{-1}$, and connected to a mass spectrometer for quantifying the permeated $H_2$.

In addition to being a diluent, the Ar in the feed gas was used as a tracer. A leak will be indicated by an increase in Ar signal in the mass spectrometer. The $H_2$ permeable membrane tubular reactor without any leakage was indicated by the measured gas profiles shown in FIG. 7A. Ideally, only $H_2$ is allowed to permeate through the dense membrane to the sweep side of the membrane tubular reactor. Before the permeation test, leakage was checked at room temperature to make sure that no pinholes or cracks were observed. In the permeation tests, if any leakage was presented, an increase in Ar signal will be observed.

Figure 7A:
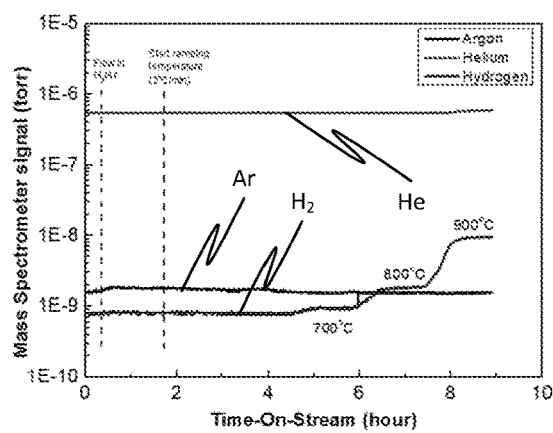
FIG. 7A is a graph of mass spectrometry signals over time for gases on a permeate side of an ideal pinhole-free membrane.
Figure 7B:
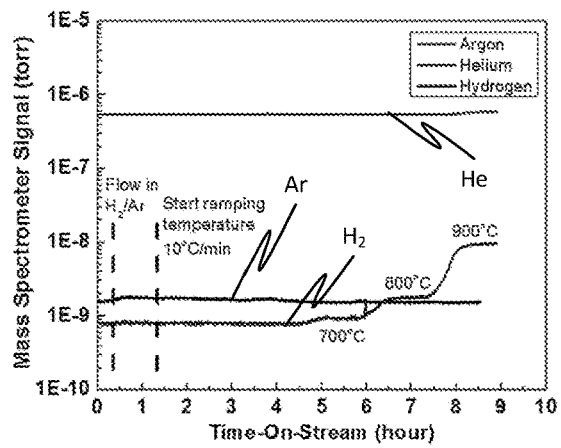
FIG. 7B is a graph of mass spectrometry signals over time for gases on a permeate side of another membrane fabricated using an optimized citrate precipitation method.

FIG. 7A demonstrates an ideal gas profile from the $H_2$ permeation experiments. At the beginning of the experiment, only He flows at the sweep side in order to establish baselines for all the gases. Once the baselines are established, the flow of feed gases ($H_2$/Ar) through the membrane reactor is initiated. Ideally, there should not be any change to the concentrations of gases in the feed and sweep sides of the membrane reactor. This signifies that the tubular membrane reactor is under leakage-free condition. If the membrane leaks, increases in both the Ar and $H_2$ signals are observed. When the membrane reactor is heated to elevated temperatures (e.g., >1000K), an increase in $H_2$ partial pressure is observed in the sweep side, which corresponds to the $H_2$ permeation through the dense $SrCe_{0.7}Zr_{0.2}Eu_{0.1}O_{3-\delta}$ ceramic membrane. The temperature is held at this temperature until the $H_2$ signal is stabilized. Afterward, the reactor temperature is further raised to the next set point. In the graphs of FIGS. 7A-7B, the $H_2$ permeation tests were conducted at 973K, 1073K, and 1173K, respectively.

While $SrCe_{0.7}Zr_{0.2}Eu_{0.1}O_{3-\delta}$ membrane synthesized via the solid state method demonstrated pinholes or cracks that caused leakage at room temperature, the citrate fabrication method described above resulted in a substantially leak-free, dense membrane. The $H_2$ permeation performance of the $SrCe_{0.7}Zr_{0.2}Eu_{0.1}O_{3-\delta}$ membrane reactor made by the citrate method is illustrated in FIG. 7B. As is apparent from the figure, no permeation of $H_2$ and Ar gases are observed at room temperature, which suggests that this is a dense membrane. When the temperature is raised, there is no evidence of Ar permeation, which can be caused, for example, by the formation of pinholes due to thermal expansion of the dense ceramic membrane on the porous support. Note that profiles of FIG. 7B are similar to those illustrated in the ideal of FIG. 7A, suggesting that a leakage-free membrane is achieved.

Figure 8A:
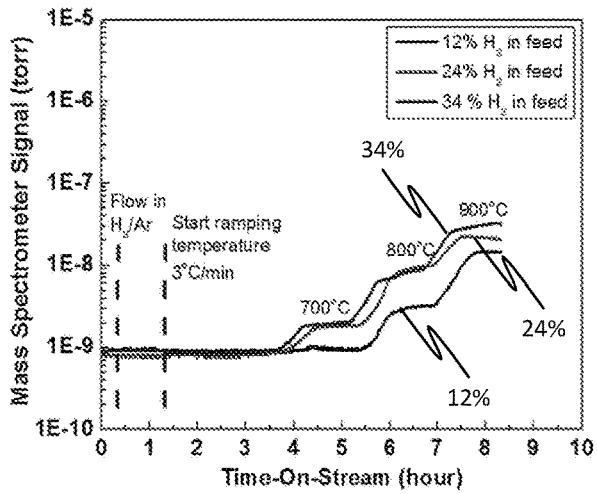
FIG. 8A is a graph of mass spectrometry signals over time for $H_2$ on a permeate side of a membrane for various temperatures and $H_2$ concentrations on a feed side of the membrane.
Figure 8B:
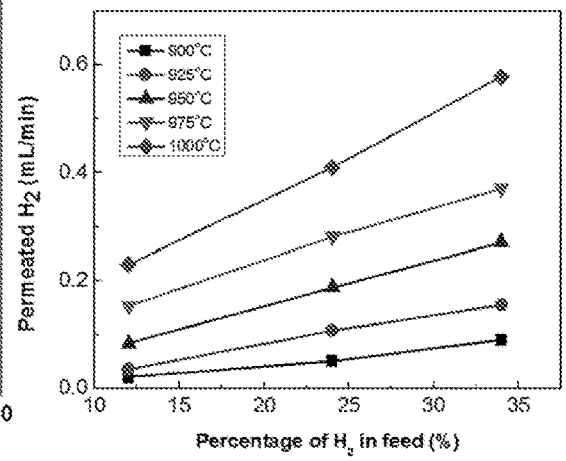
FIG. 8B is a graph of flow rate of $H_2$ on a permeate side of a membrane versus $H_2$ concentration on a feed side of the membrane for various temperatures.
Figure 8C:
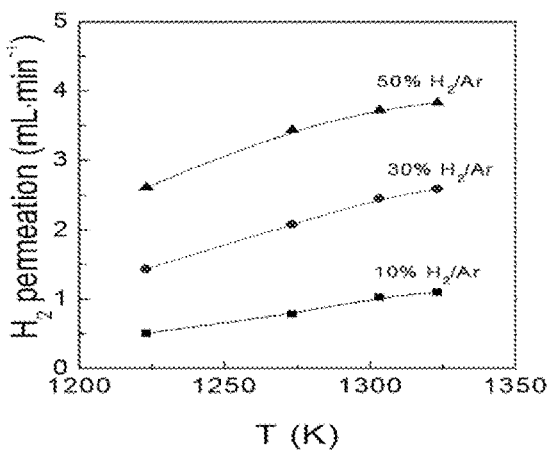
FIG. 8C is a graph of flow rate of $H_2$ on a permeate side of a membrane in a packed-bed membrane reactor versus temperature for various feed gas compositions.
Figure 8D:
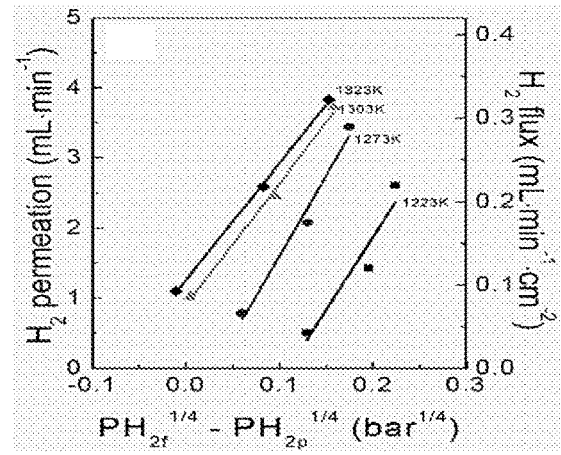
FIG. 8D is a graph of flow rate and flux of $H_2$ on a permeate side of a membrane in a packed-bed membrane reactor versus $H_2$ partial pressure on a feed gas side of the membrane.

Prior to catalysis testing, the $H_2$ permeation through the $SrCe_{0.7}Zr_{0.2}Eu_{0.1}O_{3-\delta}$ membrane in the membrane reactor was measured. FIG. 8A illustrates $H_2$ permeation as a function of temperatures and $H_2$ concentration on the feed side. FIG. 8B illustrates permeated $H_2$ flow rates in the sweep side of the $SrCe_{0.7}Zr_{0.2}Eu_{0.1}O_{3-\delta}$ membrane versus $H_2$ concentration on the feed side. FIG. 8C shows that the permeated $H_2$ flux was increased with the $H_2$ concentration on the feed side. In addition, the $H_2$ permeation flux increased as the temperature increased due to the increase in ambipolar ionic/electronic conductivity of the $SrCe_{0.7}Zr_{0.2}Eu_{0.1}O_{3-\delta}$ membrane. FIG. 8D further shows that the $H_2$ permeation flux was proportional to the transmembrane $H_2$ partial pressure gradient with a ¼ dependence.

In one or more embodiments, the catalyst can comprise metal elements doped (i.e., lattice doping) in the lattice of amorphous-molten-state materials made from Si bonded with one or two of elemental C, N or O, for example, $SiO_2$. In lattice doping, the dopant metal elements exchange with the lattice elements in the doped materials such that the metal dopant elements are confined in the lattice of the doped materials. For example, the amount of dopant metal can be between 0.001 wt % and 10 wt % of the total weight of the catalyst. For example, the dopant metal elements can be one or more of Li, Na, K, Mg, Al, Ca, Sr, Ba, Y, La, Ti, Zr, Ce, Cr, Mo, W, Re, Fe, Co, Ni, Cu, Zn, Ge, In, Sn, Pb, Bi, Mn, such as Fe.

For example, the catalyst can comprise Fe(c)$SiO_2$, which has lattice-confined single iron sites embedded in the silica matrix. The integration of the Fe(c)$SiO_2$ (containing 0.5 wt % Fe) catalyst in the $SrCe_{0.7}Zr_{0.2}Eu_{0.1}O_{3-\delta}$ membrane reactor for NDMC can enhance $CH_4$ conversion compared to that in a fixed-bed reactor. Fe(c)$SiO_2$ (containing 0.5 wt % Fe) catalyst was prepared by fusing ferrous metasilicate ($Fe_2SiO_4$) in quartz at 1973K for 6 hours, followed by leaching with aqueous nitric acid solution and drying at 343K. Alternatively or additionally, the $Fe_2SiO_4$ and $SiO_2$ can be mixed and ball-milled, for example, for 20 hours, after which it is heated to 1973K for 6 hours in stagnant air. After cooling to room temperature, the particles can be pelleted, crushed, and sieved to 40-80 mesh for use as the catalyst. The surface area of the catalyst can be <1 $m^2/g$.

The ferrous metasilicate ($Fe_2SiO_4$) can be formed, for example, via a sol-gel method. First, 375 mL toluene and 175 mL methanol are subject to reflux mixing at 120° C. (e.g., in oil bath) under $N_2$ flow for 30 min, after which 8.7 g of $FeCl_2$ (99.5% metal basis) and then 9.3 g of $NaOC_2H_5$ are added to the liquid mixture. The temperature of the oil bath is then increased to 150° C., after which 7.9 g of TEOS (98%) is added to the mixture. The solution is then allowed to reflux for 30 min, after which 10 mL of 0.2M NaOH is slowly added to the mixture (e.g., at 0.5 ml/min via syringe pump). The solution is further allowed to reflux for 12 hours, after which it is cooled to room temperature under $N_2$ flow. The cooled solution is then dried via rotary evaporator to form a powder. The powder is then subject to calcination in $N_2$ at 800° C. for 4 hours (e.g., ramp to final temperature over 2 hours and hold at final temperature for 2 hours) to produce $Fe_2SiO_4$.

Testing was also performed to evaluate percentage of methane ($CH_4$) converted and product selectivity employing Fe(c)$SiO_2$ as a catalyst. The catalyst performance tests were run at atmospheric pressure in either a packed-bed quartz tube microreactor (without permeation) or tubular membrane reactor (with $H_2$ permeation) to evaluate the methane conversion and product selectivity. In a typical experiment, 0.375 g of catalyst was loaded at the center of the reactor (e.g., in or adjacent to the first gas volume) and then heated to the desired temperature in pure Ar at a rate of 20 mL/min. Then the reaction gas mixture (90% methane, 10% Ar) was introduced over the catalyst. Temperatures during the test ranged from 1223K to 1323K. Feed gas space velocity ranged from 800 to 3200 ml-$g^{-1}$-$h^{-1}$. During tests with the tubular membrane reactor, sweep gas (e.g., He) space velocity was 3200 ml-$g^{-1}$-$h^{-1}$. Product concentration during operation was monitored by gas chromatography, while sweep gas composition (e.g., in or from the second gas volume) was monitored via mass spectrometry.

Figure 9A:
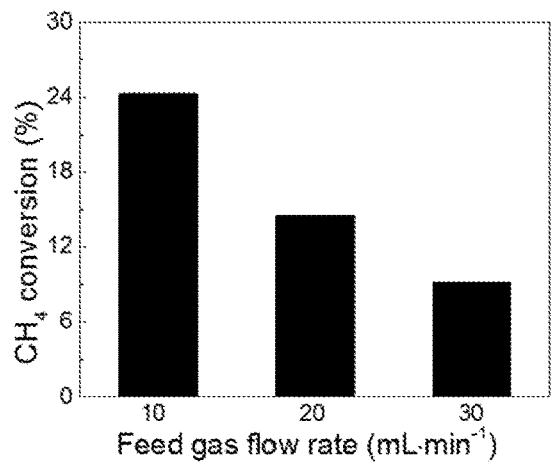
FIG. 9A is a graph of methane conversion percentage versus feed space velocity of methane for an $Fe(c)SiO_2$ catalyst in a fixed-bed reactor.
Figure 9B:
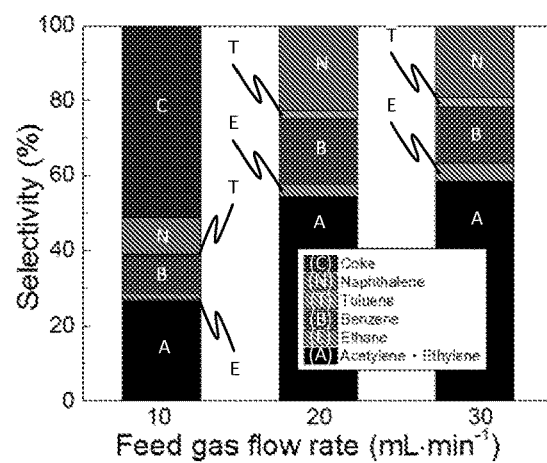
FIG. 9B is a graph of conversion product selectivity versus feed space velocity of methane for an $Fe(c)SiO_2$ catalyst in a fixed-bed reactor.
Figure 9C:
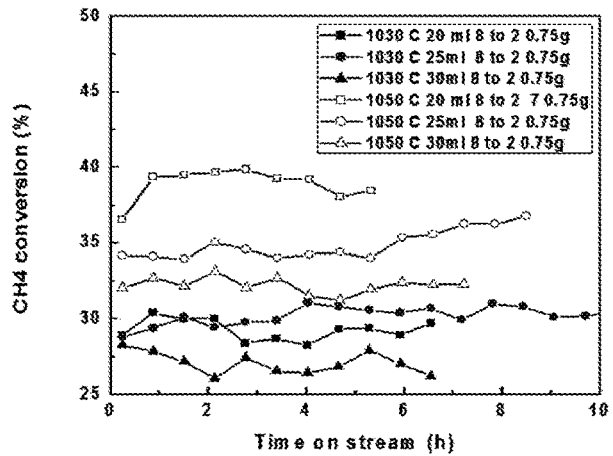
FIG. 9C is a graph of methane conversion percentage versus time on stream for an $Fe(c)SiO_2$ catalyst in a fixed-bed reactor for various reaction temperatures, catalyst loadings, and flow rates.

FIGS. 9A-9B shows methane conversion and product selectivity, respectively, versus methane feed gas flow rate for a fixed bed reactor using Fe(c)$SiO_2$ catalyst. FIG. 9C shows methane conversion versus time for affixed bed reactor using Fe(c)$SiO_2$ catalyst for different reaction temperatures and feed gas flow rate. By decreasing the space velocity of the feed rate, the residence time is increased, and therefore leads to higher methane conversion, as shown, for example, by FIG. 9A. Varying the space velocity of the feed rate also has an effect on the product selectivity, as shown, for example, by FIG. 9B. By lowering the space velocity, the residence time is increased, and, therefore the selectivity toward larger molecule aromatics (e.g., benzene, naphthalene) is increased. On the other hand, by increasing the space velocity, the selectivity toward smaller molecules (e.g., $C_2$) is increased. However, if the space velocity is too low, carbon deposition (e.g., coke) is formed.

Optimal flow rate for methane conversion may be dependent on temperature, as illustrated by FIG. 9C, where 25 mL/min produces higher methane conversion than 20 mL/min or 30 mL/min for 1030° C. reaction temperature while 20 mL/min produces higher methane conversion than 25 mL/min or 30 mL/min for 1050° C. reaction temperature. Note that in FIG. 9C the selectivity to aromatics (e.g., benzene of about 15% and naphthalene of about 50%) is about the same for each temperature.

Figure 10:
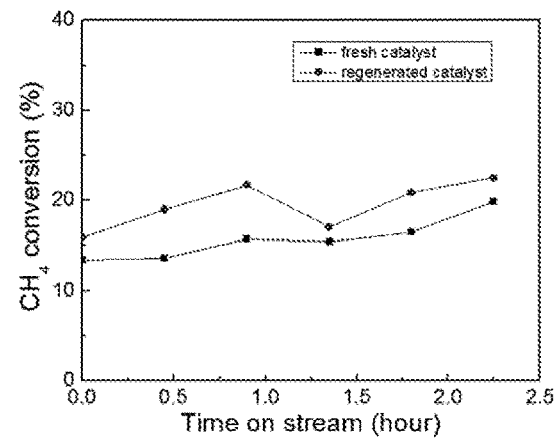
FIG. 10 is a graph of methane conversion percentage versus time on stream for a fresh $Fe(c)SiO_2$ catalyst and a regenerated $Fe(c)SiO_2$ catalyst in a fixed-bed reactor.

The regeneration capability of the Fe(c)$SiO_2$ catalysts was also tested in NDMC reactions. The used catalyst was heated in air stream to burn off coke or other heavy hydrocarbon deposits. In the regeneration process, dry air was introduced to the catalyst bed at a space velocity between 3200 mL-$g^{-1}$-$h^{-1}$ and 4840 mL $g^{-1}$ $h^{-1}$ at a temperature of 800° C. for 4 hours. FIG. 10 compares the performance of the fresh and regenerated Fe(c)$SiO_2$ catalyst. It can be seen that the methane conversion between the two catalysts are very similar, and therefore proves that regeneration does not diminish the effectiveness of the Fe(c)$SiO_2$ catalyst for the methane conversion reactions.

Figure 11A:
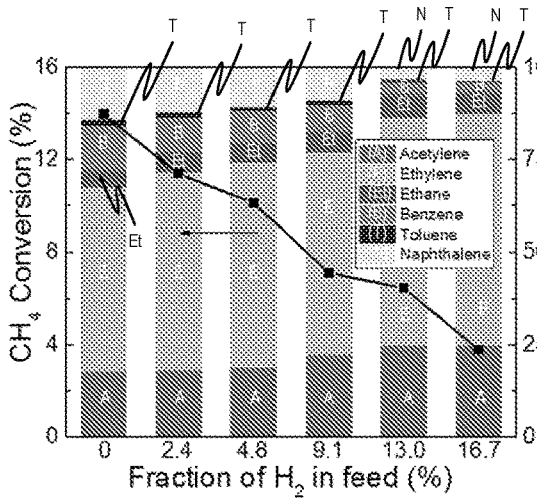
FIG. 11A is a graph of methane conversion percentage (left axis) and conversion product selectivity (right axis) versus $H_2$ feed fraction for an $Fe(c)SiO_2$ catalyst in a fixed-bed reactor, at a reaction temperature of 1303K and feed gas space velocity of 3200 mL-$g^{-1}$-$h^{-1}$.
Figure 11B:
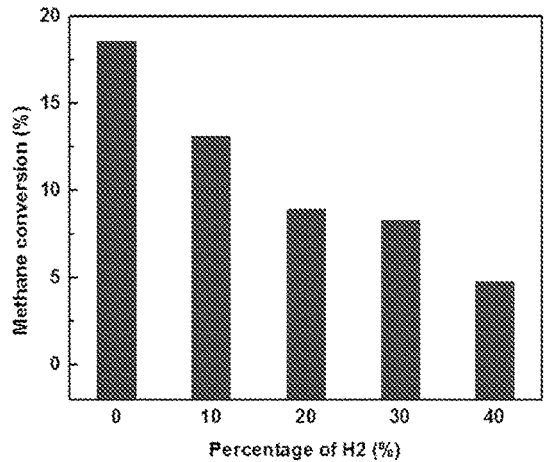
FIG. 11B is a graph of methane conversion percentage versus $H_2$ feed fraction for an $Fe(c)SiO_2$ catalyst in a fixed-bed reactor, at a reaction temperature of 1303K and feed gas flow rates of 20 mL/min.
Figure 11C:
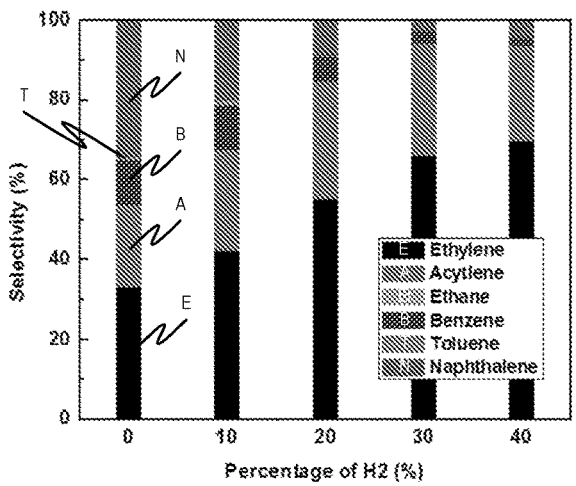
FIG. 11C is a graph of conversion product selectivity versus $H_2$ feed fraction for an $Fe(c)SiO_2$ catalyst in a fixed-bed reactor, at a reaction temperature of 1303K and feed gas flow rates of 20 mL/min.

FIGS. 11A-11C show measured methane conversion and product selectivity over Fe(c)$SiO_2$ catalyst when the fraction of $H_2$ in the feed stream was varied. The increase in $H_2$ concentration in the feed stream increased the $C_2$ (i.e., acetylene and ethylene) selectivity from 65% to 88%, while the methane conversion was decreased from ~15% to 4% for $H_2$ fractions from 0% to 16.7%. In comparison to adding $H_2$ to the permeate sweep side of the reactor (data shown in FIG. 15B), the increase in $C_2$ selectivity with $H_2$ on feed side significantly decreased the methane conversion. With increasing $H_2$ partial pressure, methane conversion decreases, aromatic selectivity decreases, and $C_2$ selectivity increases. Overall, the $H_2$ permeable membrane reactor shows a great potential in shifting the product selectivity to $C_2$ products while maintaining methane conversion (i.e., product yield) in the non-oxidative methane conversation chemistry.

Figure 12A:
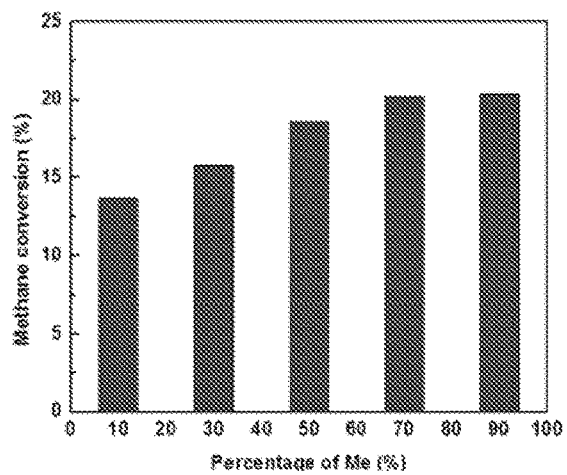
FIG. 12A are graph of methane conversion percentage versus methane feed fraction for an $Fe(c)SiO_2$ catalyst in a fixed-bed reactor, at a reaction temperature of 1303K and feed gas flow rate of 20 mL/min.
Figure 12B:
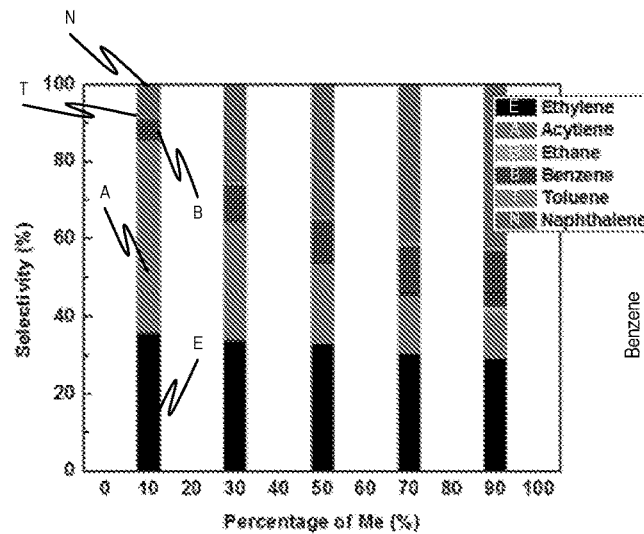
FIG. 12B is a graph of conversion product selectivity versus methane feed fraction for an $Fe(c)SiO_2$ catalyst in a fixed-bed reactor, at a reaction temperature of 1303K and feed gas flow rate of 20 mL/min.
Figure 13A:
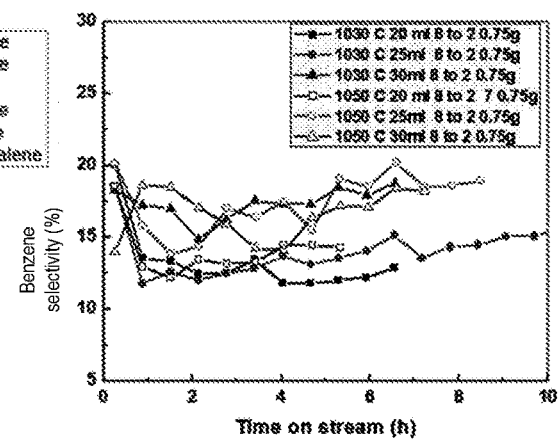
FIGS. 13A-13E are graphs of benzene, naphthalene, acetylene, ethylene, and ethane fractions of conversion products over time, respectively, for an $Fe(c)SiO_2$ catalyst in a fixed-bed reactor, at various reaction temperatures and feed gas flow rates.
Figure 13B:
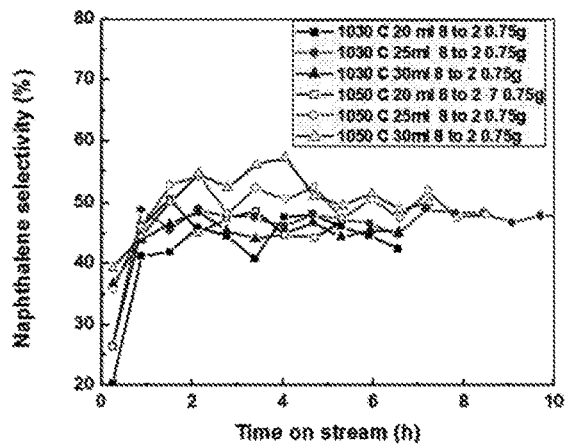
Figure 13C:
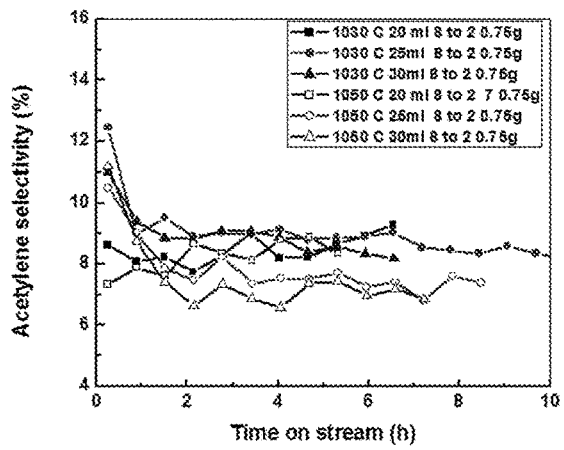
Figure 13D:
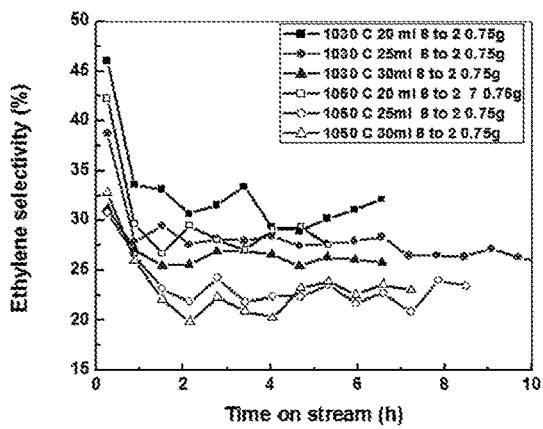
Figure 13E:
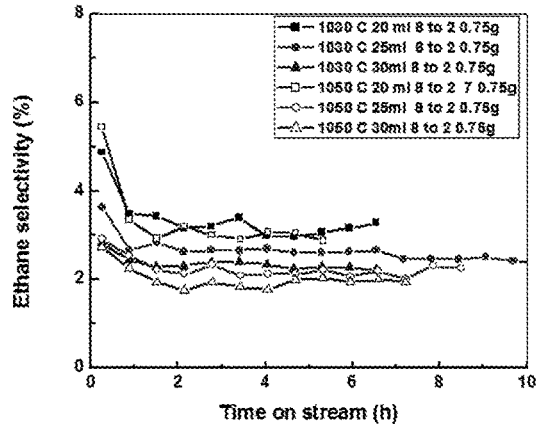

FIGS. 12A-12B show measured methane conversion and product selectivity over Fe(c)$SiO_2$ catalyst in a fixed-bed reactor when methane partial pressure is varied in the feed flow. With increase of methane partial pressure, methane conversion increases and then remains stable. Aromatics selectivity increases while $C_2$ selectivity decreases. FIGS. 13A-13E are graphs of benzene, naphthalene, acetylene, ethylene, and ethane fractions of conversion products over time, respectively, for an Fe(c)$SiO_2$ catalyst in a fixed-bed reactor, at various reaction temperatures and feed gas flow rates. The selectivity to aromatics (e.g., benzene ~15%, naphthalene ~50%) remains about the same for each temperature, while the selectivity to light hydrocarbons (e.g., $C_2$) decreases with increasing temperature and methane flow rate.

Figure 14A:
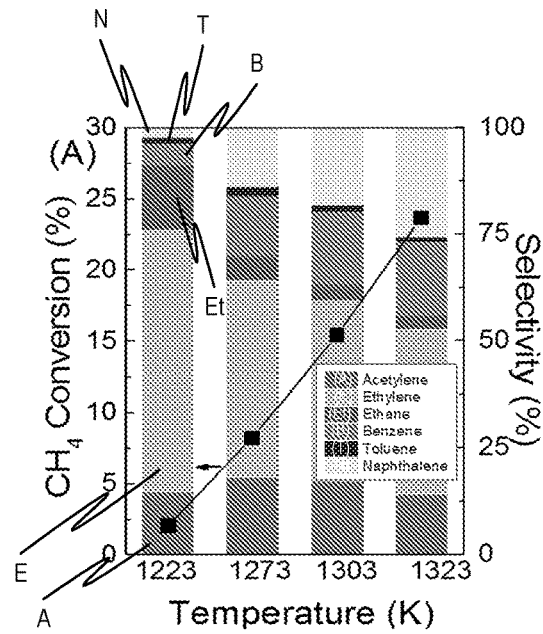
FIG. 14A is a graph of methane conversion percentage (left axis) and conversion product selectivity (right axis) versus reaction temperature for an $Fe(c)SiO_2$ catalyst in a fixed-bed reactor, at a feed gas space velocity of 3200 mL-$g^{-1}$-$h^{-1}$.
Figure 14B:
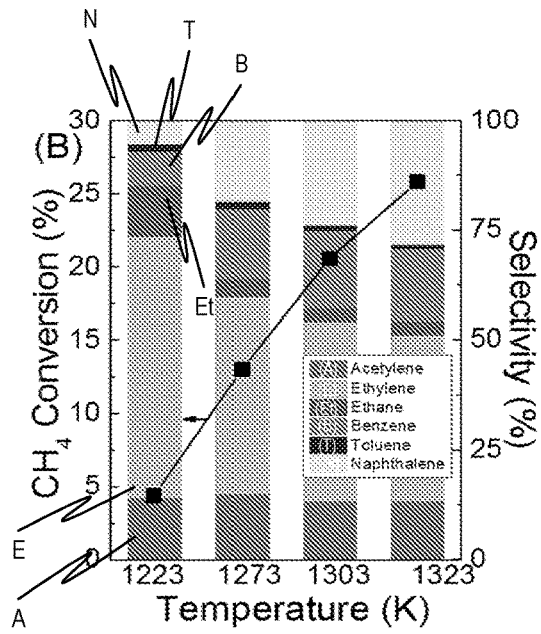
FIG. 14B is a graph of methane conversion percentage (left axis) and conversion product selectivity (right axis) versus reaction temperature for an $Fe(c)SiO_2$ catalyst in a packed-bed membrane reactor, at a feed gas space velocity of 3200 mL-$g^{-1}$-$h^{-1}$.

FIGS. 14A-14B show methane conversion percentage and conversion product selectivity versus reaction temperature for an Fe(c)$SiO_2$ catalyst in a fixed-bed reactor and packed-bed membrane reactor, respectively. In the fixed-bed reactor (FIG. 14A), the reaction was very selective toward $C_2$ (i.e., ethylene, acetylene and ethane, ~90%), and only small amount of aromatics (<~10%) were formed at 1223K. As the temperature increases, the selectivity shifts from smaller $C_2$ products to aromatics (i.e., benzene, toluene and naphthalene). Comparing the temperature of 1323K to 1223K, the selectivity of $C_2$ for the fixed-bed reactor lowered from ~90% to ~55%, while the aromatics content increased from ~10% to ~45%.

Comparing the product selectivity between the fixed-bed reactor (FIG. 14A) and the $H_2$ permeable membrane reactor (FIG. 14B), the membrane reactor was slightly less selective for $C_2$ and more selective for aromatic products. The yields for both $C_2$ and aromatics of the membrane reactor are higher at all temperatures tested as compared to the fixed-bed reactor. An increase in methane conversion with increasing temperature was observed in both types of reactors due to the endothermic nature of the NDMC reaction.

The packed-bed membrane reactor enabled higher methane conversion in a range of 5% to 25% compared to the fixed-bed membrane reactor when the temperature was raised from 1223K to 1323K. The He sweep gas flow rate was controlled at 20 mL·min$^{-1}$ in each reaction condition. The simultaneous removal of $H_2$ from the membrane reactor shifted the reaction to the product side. The higher $H_2$ permeation flux at higher temperature and higher $H_2$ partial pressure differences is expected, which should lead to a higher degree increase in methane conversions.

Figure 15A:
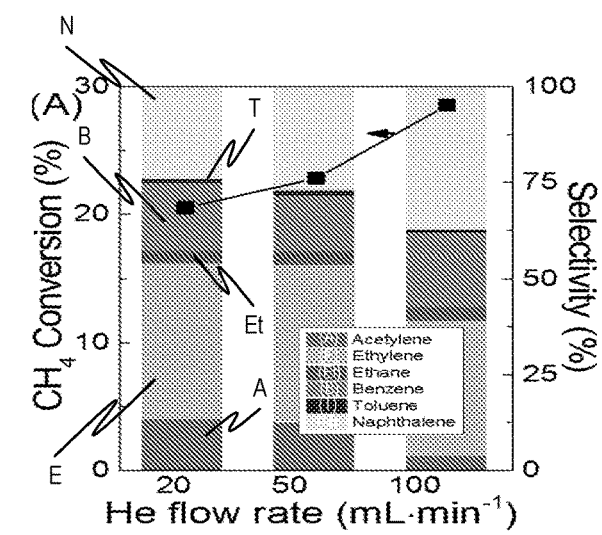
FIG. 15A is a graph of methane conversion percentage (left axis) and conversion product selectivity (right axis) versus He sweep gas flow rate for an $Fe(c)SiO_2$ catalyst in a packed-bed membrane reactor, at a reaction temperature of 1303K and a feed gas space velocity of 3200 mL-$g^{-1}$-$h^{-1}$.
Figure 15B:
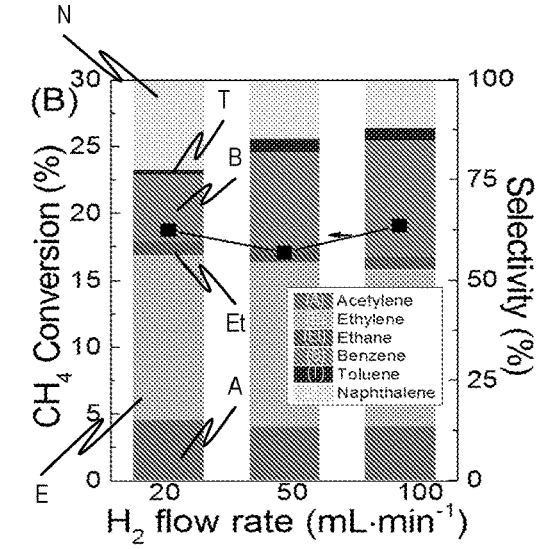
FIG. 15B is a graph of methane conversion percentage (left axis) and conversion product selectivity (right axis) versus $H_2$ sweep gas flow rate for an $Fe(c)SiO_2$ catalyst in a packed-bed membrane reactor, at a reaction temperature of 1303K and a feed gas space velocity of 3200 mL-$g^{-1}$-$h^{-1}$.

FIGS. 15A-15B show methane conversion percentage and conversion product selectivity versus He and $H_2$ sweep gas flow rates, respectively, for an Fe(c)SiO$_2$ catalyst in a packed-bed membrane reactor. The manipulation of the sweep side environment influences the catalysis chemistry inside the membrane reactor. As shown in FIG. 15A, $CH_4$ conversion increased with an increase of He flow to 50 mL/min and doubled at 100 mL/min He flow compared to that in a fixed-bed reactor. The high sweep He flow carries away more $H_2$ through the membrane reactor. For comparison, $H_2$ was purposely added back to the membrane reactor by flowing $H_2$ as the sweep gas. As shown in FIG. 15B, the $CH_4$ conversion was slightly reduced because the reaction was shifted to the reactant side.

In view of FIGS. 15A-15B, it is apparent that the conversion efficiency and/or product selectivity can be regulated by controlling the sweep gas composition and/or flow rate. For example, the selectivity to naphthalene can be increased by increasing He flow rate, as per FIG. 15A. In another example, the selectivity to $C_2$ and benzene products can be increased by increasing $H_2$ flow rates, as per FIG. 15B. The slight sacrifice of methane conversion to provide tuning to $C_2$ and benzene products versus naphthalene is unique for the NDMC reactions in the $H_2$ permeable SrCe$_{0.7}$Zr$_{0.2}$Eu$_{0.1}$O$_{3-\delta}$ membrane reactor. On the other hand, an increase in methane conversion and aromatic product formation were achieved with the packed-bed $H_2$ permeable membrane reactor with He sweep gas flow. Both ends of products are attractive chemicals used in industry.

The stability of the Fe(c)SiO$_2$ catalyst in NDMC reaction in the $H_2$ permeable membrane reactor was tested by running the reaction at 1303 K for 20 hours. As illustrated in FIG. 16, no obvious deactivation was observed during the test. Indeed, the $CH_4$ conversion remained at ~20% throughout the test, with substantially constant product selectivity to $C_2$ (65%), benzene (18%) and naphthalene (15%). Overall selectivity to these value-added products remained at greater than 99% during the test, with substantially no production (i.e., <1%) of coke and/or carbon dioxide.

FIGS. 17A-17B show methane conversion percentage and conversion product selectivity, respectively, versus fraction of $C_2H_6$ in the feed gas for an Fe(c)SiO$_2$ catalyst in a fixed-bed reactor. As shown in FIG. 17A, $CH_4$ conversion increased as $C_2H_6$ partial pressure increased, up to a $C_2H_6$ percentage of 10%, after which the $CH_4$ conversion decreases with increasing $C_2H_6$ partial pressure. As shown in FIG. 17B, the reaction selectivity to benzene increases as $C_2H_6$ partial pressure increases, while selectivity to naphthalene remains relatively stable regardless of $C_2H_6$ partial pressure. Note that selectivity to $C_2$ hydrocarbons decreases as $C_2H_6$ partial pressure increases.

Figure 18A:
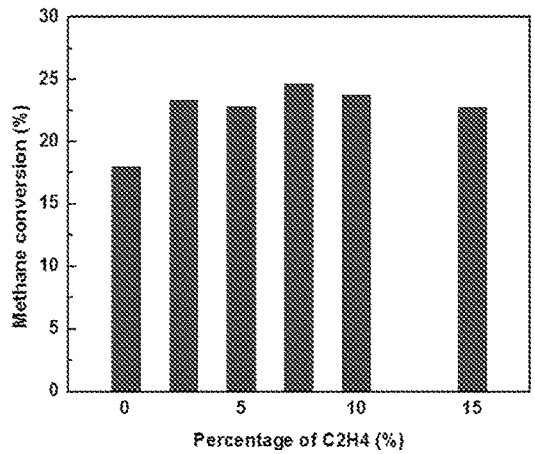
FIG. 18A is a graph of methane conversion percentage versus $C_2H_4$ feed fraction for an $Fe(c)SiO_2$ catalyst in a fixed-bed reactor, at a reaction temperature of 1303K and feed gas flow rates of 20 mL/min.
Figure 18B:
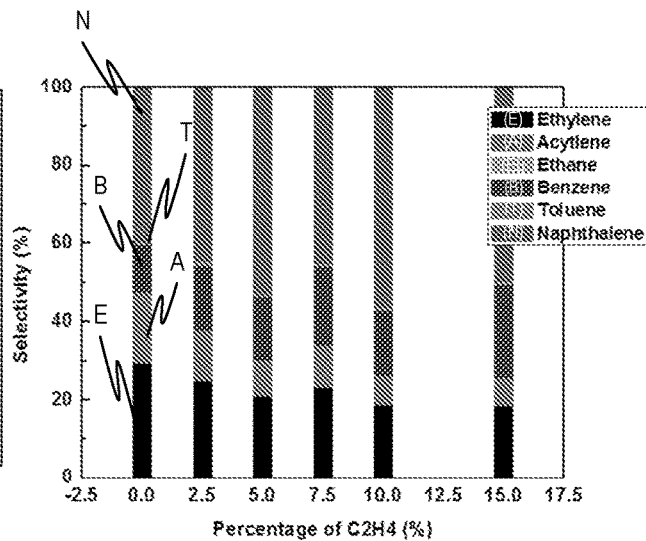
FIG. 18B is a graph of conversion product selectivity versus $C_2H_4$ feed fraction for an $Fe(c)SiO_2$ catalyst in a fixed-bed reactor, at a reaction temperature of 1303K and feed gas flow rates of 20 mL/min.

FIGS. 18A-18B show methane conversion percentage and conversion product selectivity, respectively, versus fraction of $C_2H_4$ in the feed gas for an Fe(c)SiO$_2$ catalyst in a fixed-bed reactor. As shown in FIG. 18A, $CH_4$ conversion increased as $C_2H_4$ partial pressure increased, up to a $C_2H_4$ percentage of about 2.5%, after which the $CH_4$ conversion remains substantially the same despite increasing $C_2H_4$ partial pressure. As shown in FIG. 18B, the reaction selectivity to benzene increases as $C_2H_4$ partial pressure increases, while selectivity to naphthalene remains relatively stable regardless of $C_2H_4$ partial pressure. Note that selectivity to $C_2$ hydrocarbons decreases as $C_2H_4$ partial pressure increases.

Figure 19A:
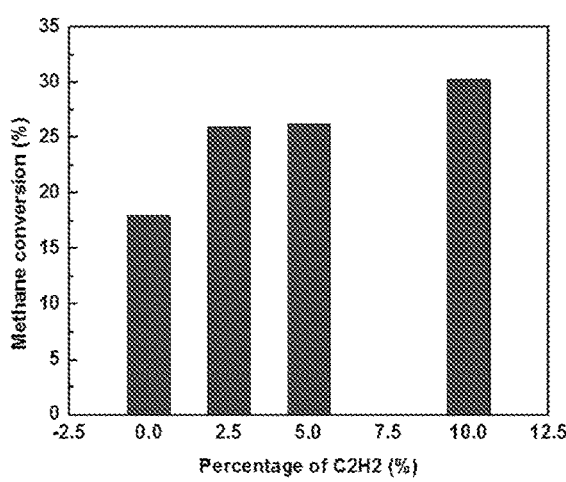
FIG. 19A is a graph of methane conversion percentage versus $C_2H_2$ feed fraction for an $Fe(c)SiO_2$ catalyst in a fixed-bed reactor, at a reaction temperature of 1303K and feed gas flow rates of 20 mL/min.
Figure 19B:
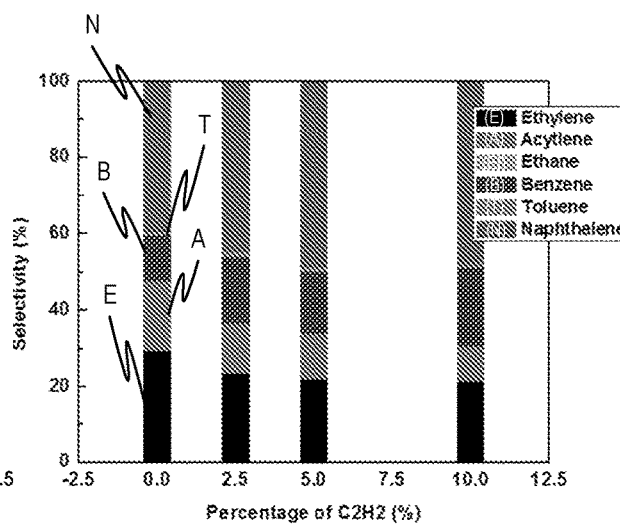
FIG. 19B is a graph of conversion product selectivity versus $C_2H_2$ feed fraction for an $Fe(c)SiO_2$ catalyst in a fixed-bed reactor, at a reaction temperature of 1303K and feed gas flow rates of 20 mL/min.

FIGS. 19A-19B show methane conversion percentage and conversion product selectivity, respectively, versus fraction of $C_2H_2$ in the feed gas for an Fe(c)SiO$_2$ catalyst in a fixed-bed reactor. As shown in FIG. 19A, $CH_4$ conversion increased as $C_2H_2$ partial pressure increased. As shown in FIG. 19B, the reaction selectivity to benzene increases as $C_2H_2$ partial pressure increases, while selectivity to naphthalene remains relatively stable regardless of $C_2H_2$ partial pressure. Note that selectivity to $C_2$ hydrocarbons decreases as $C_2H_2$ partial pressure increases.

In view of FIGS. 15A-19B, it is apparent that the conversion efficiency and/or product selectivity can be further regulated by controlling the secondary feed gas (e.g., $H_2$, $C_2H_2$, $C_2H_4$, $C_2H_6$, etc.) and/or the partial pressure of the secondary feed gas. Although specific secondary feed gases have been used in FIGS. 15A-19B, embodiments of the disclosed subject matter are not limited thereto. Alternatively or additionally, the secondary feed gases can include higher hydrocarbons and aromatics, such as, but not limited to, propane, butane, heptane, benzene, toluene, xylene, or an impurity hydrocarbon from shale gas.

In embodiments of the disclosed subject matter, the variables of feed gas flow rate and composition (constituents and partial pressures), sweep gas flow rate and composition (constituents and partial pressures), and reaction temperature can be regulated, for example, by a controller or system operator, to produce a desired selection of products and/or conversion efficiency by the methane conversion reactor.

Although the discussion above is directed to the Fe(c)SiO$_2$ catalyst, embodiments of the disclosed subject matter are not limited thereto. Rather, other catalysts may be used according to one or more contemplated embodiments. For example, an alternative catalyst can be a metal/zeolite catalyst. The metal can comprise one or more of molybdenum (Mo), rhenium (Re), zirconium (Zr), zinc (Zn), and tungsten (W). The zeolite can be MFI (ZSM5), MWW, BEA, or MOR. For example, the alternative catalyst can be Mo/ZSM5. Such a catalyst can be created with variable meso-/microporosity, with zeolite porosity optimized for methane conversion, for example, using a dual-template assisted synthesis method, an incipient wetness impregnation method, or any other method known in the art.

In one or more first embodiments, a method of converting methane includes flowing methane in a first volume so as to contact a catalyst in a reactor while heating the reactor to an elevated temperature, and transporting $H_2$ from the first volume to a second volume in the reactor via a membrane supported within the reactor.

In the first embodiments or any other disclosed embodiment, the products can be removed from the first volume, for example, for subsequent use, recirculation, and/or storage.

In the first embodiments or any other disclosed embodiment, the products can comprise the products comprise $C_2$ hydrocarbons and/or aromatics. In the first embodiments or any other disclosed embodiment, the products can consist essentially of $C_2$ hydrocarbons and/or aromatics. In the first embodiments or any other disclosed embodiment, neither carbon dioxide nor coke is formed by the method, and/or less than 1% of other hydrocarbon products are formed by the method.

In the first embodiments or any other disclosed embodiment, the flow into the first volume consists essentially of methane. Alternatively, the flow into the first volume includes one or more gases in addition to methane are flowed into the first volume. In the first embodiments or any other disclosed embodiment, the one or more gases is at least one of $H_2$, $C_2H_2$, $C_2H_4$, $C_2H_6$, and higher hydrocarbons and aromatics. In the first embodiments or any other disclosed embodiment, the method further includes adjusting a partial pressure of the one or more gases to regulate a percentage of methane converted and/or a selectivity of the methane conversion to one or more of the products.

In the first embodiments or any other disclosed embodiment, the catalyst comprises a metal doped in a quartz lattice. In the first embodiments or any other disclosed embodiment, the metal comprises at least one of Li, K, Mg, Al, Ca, Sr, Ba, Ti, Ce, Mn, Zn, Co, Ni, and Fe. In the first embodiments or any other disclosed embodiment, the catalyst comprises $Fe(c)SiO_2$. In the first embodiments or any other disclosed embodiment, the catalyst comprises metal/zeolite. In the first embodiments or any other disclosed embodiment, the metal of the catalyst can be Mo, Re, Zr, Zn, or W, and the zeolite can be MFI (ZSM5), MWW, BEA, or MOR. In the first embodiments or any other disclosed embodiment, the catalyst comprises Mo/ZSM5.

In the first embodiments or any other disclosed embodiment, the membrane is a ceramic or ceramic metal composite that conducts protons and electrons. In the first embodiments or any other disclosed embodiment, the membrane comprises a perovskite-type oxide having a formula of $M'Ce_{1-x-y}Zr_xM''_yO_{3-\delta}$, where M' is a least one of Sr and Ba, M'' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb, x is between 0.1 and 0.2, inclusive, and y is between 0.1 and 0.3, inclusive. In the first embodiments or any other disclosed embodiment, the membrane is formed of $SrCe_{0.7}Zr_{0.2}Eu_{0.1}O_{3-\delta}$.

In the first embodiments or any other disclosed embodiment, the membrane is disposed on a surface of a porous support, which can comprise a material that is the same or different than the membrane. In the first embodiments or any other disclosed embodiment, the membrane and the porous support have coefficients of thermal expansion that are substantially the same. In the first embodiments or any other disclosed embodiment, the porous support comprises a perovskite-type oxide having a formula of $M'Ce_{1-x}Zr_xO_{3-\delta}$, where M' is Sr or Ba, and x is between 0.1 and 0.3, inclusive. In the first embodiments or any other disclosed embodiment, the porous support is formed of $SrCe_{0.8}Zr_{0.2}O_3$. In the first embodiments or any other disclosed embodiment, the membrane and/or the porous support is a perovskite-type oxide represented by the general formula $ABO_3$, where A is at least one element selected from the group consisting of Ba, Ca, Mg and Sr; B is $Ce_{1-x}M_x$ or $Zr_{1-x}M_x$; M is a multivalent dopant metal, for example, an element selected from the group consisting of Y, Yb, In, Gd, Nd, Eu, Sm and Tb; and x is greater than 0 and less than 1, for example, between 0.05 and 0.40, inclusive.

In the first embodiments or any other disclosed embodiment, the second volume is separated from the first volume by the membrane. In the first embodiments or any other disclosed embodiment, the transporting $H_2$ through the membrane is via ion transport without an externally applied electric field.

In the first embodiments or any other disclosed embodiment, the method also includes, at a same time as the flowing a reactant gas, flowing a sweep gas in the second volume to remove the transported $H_2$ therefrom and/or to react with the transported $H_2$ therein. In the first embodiments or any other disclosed embodiment, the sweep gas can be $H_2$, air, steam, $N_2$, $CO_2$, CO, and/or a noble gas. In the first embodiments or any other disclosed embodiment, the method can also include adjusting an amount of $H_2$ in the sweep gas to regulate a selectivity of the methane conversion to one or more of the products. In the first embodiments or any other disclosed embodiment, the method can further include adjusting a flow rate of the sweep gas to regulate a percentage of methane converted and/or a selectivity of the methane conversion to one or more of the products.

In the first embodiments or any other disclosed embodiment, the method can further include reacting the transported $H_2$ with the sweep gas to form a secondary product. In the first embodiments or any other disclosed embodiment, the sweep gas is air or steam, and the secondary product comprises water. In the first embodiments or any other disclosed embodiment, the method can further include heating the reactor using heat from the reaction between the transported $H_2$ and the sweep gas. In the first embodiments or any other disclosed embodiment, the sweep gas is $CO_2$ or CO, and the secondary product comprises syngas, methanol, di-methyl ether, higher alcohols, and/or additional hydrocarbons. In the first embodiments or any other disclosed embodiment, the transported $H_2$ in the second volume contacts a second catalyst comprising at least one of Ni, Fe, Cu, Zn, and a metal oxide support.

In the first embodiments or any other disclosed embodiment, the method further includes adjusting a space velocity of the methane flow in the first volume to regulate a percentage of methane converted. In the first embodiments or any other disclosed embodiment, the method further includes adjusting a partial pressure of the methane flow in the first volume to regulate a selectivity of the methane conversion to one or more of the products.

In the first embodiments or any other disclosed embodiment, the membrane has a thickness of 50 µm or less, the $H_2$ being transported through the thickness. In the first embodiments or any other disclosed embodiment, the membrane has a thickness of 30 µm or less, for example, approximately 22 µm thick, the $H_2$ being transported through the thickness. In the first embodiments or any other disclosed embodiment, the membrane is substantially pinhole-free from room temperature to said elevated temperature (e.g., >873K).

In the first embodiments or any other disclosed embodiment, the reactor comprises an inner end-capped support tube and an outer tube surrounding the inner support tube. The first volume is one of an interior of the inner support tube and an annular volume between the inner and outer tubes, and the second volume is the other of the interior of the inner support tube and the annular volume between the inner and outer tubes.

In the first embodiments or any other disclosed embodiment, the reactor comprises an inner support tube and an outer tube surrounding the inner support tube. The first volume is one of an interior of the inner support tube and an annular volume between the inner and outer tubes, and the second volume is the other of the interior of the inner support tube and the annular volume between the inner and outer tubes.

In the first embodiments or any other disclosed embodiment, the first volume is the interior of the inner support tube, and the membrane is disposed on an outer surface of the inner support tube. In the first embodiments or any other disclosed embodiment, at least a portion of the interior of the inner support tube is packed with the catalyst.

In the first embodiments or any other disclosed embodiment, the first volume is the annular volume between the inner and outer tubes, and the membrane is disposed on an inner surface of the inner support tube. In the first embodiments or any other disclosed embodiment, at least a portion of an interior of the outer tube is packed with the catalyst. In the first embodiments or any other disclosed embodiment, at least a portion of the outer tube is formed of the catalyst.

In the first embodiments or any other disclosed embodiment, the reactor comprises an inner support tube, an inlet tube having an outlet within the inner support tube, and an outer tube surrounding the inner support tube. The first volume is one of an interior of the inner support tube and an annular volume between the inner and outer tubes, and the second volume is the other of the interior of the inner support tube and the annular volume between the inner and outer tubes.

In the first embodiments or any other disclosed embodiment, the membrane is disposed on a surface of the inner support tube adjacent to the second volume. In the first embodiments or any other disclosed embodiment, at least a portion of the inlet tube is formed of the catalyst, and the first volume is the interior of the inner support. In the first embodiments or any other disclosed embodiment, at least at portion of the outer tube is formed of the catalyst and the first volume is the annular volume between the inner and outer tubes.

In the first embodiments or any other disclosed embodiment, portions of the reactor (e.g., the outer tube, the inner tube, and/or the inlet tube) can be formed of a material that can tolerate the elevated temperature and potentially elevated pressures. In the first embodiments or any other disclosed embodiment, said portions of the reactor are formed of a material other than quartz, for example, a metal.

In the first embodiments or any other disclosed embodiment, the reactor is heated to a temperature of at least 873K.

In the first embodiments or any other disclosed embodiment, the method further includes providing the reactor. The membrane of the reactor can be formed by a process including forming a powder via a citrate precipitation method, forming a paste from the powder, applying the paste to a support, and sintering the support.

In the first embodiments or any other disclosed embodiment, the forming a powder includes dissolving stoichiometric amounts of $Ce(NO_3)_3 \cdot 6H_2O$, $Sr(NO_3)$, $ZrO(NO_3)_2 \cdot H_2O$, and $Eu(NO_3)_3 \cdot 6H_2O$ in solution, and optionally with other cations; adding citric acid and ethylene glycol to the solution; heating to a first temperature to evaporate solvent from the solution so as to form a gel; heating to a second temperature greater than the first temperature to combust the gel; ball milling the combusted gel followed by drying and grinding; and heating to a third temperature greater than the second temperature to form a ceramic.

In the first embodiments or any other disclosed embodiment, the forming a paste includes ball milling the powder with a solvent; combining the ball-milled powder with an ester-alcohol based material that includes a binder and a plasticizer; and evaporating the solvent to form the paste. In the first embodiments or any other disclosed embodiment, the applying the paste to a support includes diluting the paste in a solvent; coating the support in the diluted paste; and drying the coated support. In the first embodiments or any other disclosed embodiment, the coating and drying are performed more than once to provide a multi-layer coating forming the membrane.

In one or more second embodiments, a methane conversion device includes a reactor, a membrane, and a catalyst. The reactor has first and second gas volumes separated by the membrane. The catalyst is disposed to interact with gas of the first gas volume. The membrane is constructed to transport $H_2$ between the first and second gas volumes.

In the second embodiments or any other disclosed embodiment, the device can further include a controller configured to control at least one of space velocity, concentration, and composition of a first gas flow provided to the first gas volume and of a second gas flow provided to the second gas volume.

In the second embodiments or any other disclosed embodiment, the device can further include a heating module that heats the reactor to an elevated temperature (e.g., at least 873K) while methane flows within the reactor. In the second embodiments or any other disclosed embodiment, the heating module captures heat from an exothermic reaction of gases in the second gas volume for heating the reactor. In the second embodiments or any other disclosed embodiment, the heating module includes a furnace with the reactor sealed therein and/or a heating element.

In the second embodiments or any other disclosed embodiment, the catalyst comprises a metal doped in a quartz lattice or a metal/zeolite material. In the second embodiments or any other disclosed embodiment, the metal comprises at least one of Li, K, Mg, Al, Ca, Sr, Ba, Ti, Ce, Mn, Zn, Co, Ni, and Fe.

In the second embodiments or any other disclosed embodiment, the membrane is a ceramic or ceramic metal composite that conducts protons and electrons. In the second embodiments or any other disclosed embodiment, the membrane is a perovskite-type oxide having a formula of $M'Ce_{1-x-y}Zr_xM''_yO_{3-\delta}$, where M' is a least one of Sr and Ba, M" is at least one of Ti, V, Cr, Mn, Fe, Co Ni, Cu, Nb, Mo, W, Pr, Nd, Pm, Sm, Eu, Gd, Tb, Dy, Ho, Er, Tm and Yb, x is between 0.1 and 0.2, inclusive, and y is between 0.1 and 0.3, inclusive.

In the second embodiments or any other disclosed embodiment, the device further includes a porous support upon which the membrane is disposed, and the membrane is on a second-gas-volume side of the support. In the second embodiments or any other disclosed embodiment, the membrane and the porous support have coefficients of thermal expansion that are substantially the same. In the second embodiments or any other disclosed embodiment, the porous support is a perovskite-type oxide having a formula of $M'Ce_{1-x}Zr_xO_{3-\delta}$, where M' is Sr or Ba, and x is between 0.1 and 0.3, inclusive.

In the second embodiments or any other disclosed embodiment, the device further includes one or more sensors for monitoring space velocity, gas composition, and/or gas concentration to or from the first and second gas volumes.

In the second embodiments or any other disclosed embodiment, a second catalyst is disposed to interact with gas of the second gas volume and comprising a metal/metal oxide catalyst. In the second embodiments or any other disclosed embodiment, the metal of the second catalyst includes at least one of Ni, Cu, Zn, and Fe, and the metal oxide of the second catalyst includes at least one of $SiO_2$, $Al_2O_3$, $ZrO_2$, and $CeO_2$.

In the second embodiments or any other disclosed embodiment, the membrane has a thickness of 50 µm or less, for example, 30 µm or less, such as, but not limited to, approximately 22 µm.

In the second embodiments or any other disclosed embodiment, the reactor is a tubular reactor comprising a first tube and a second tube. The first tube is open at one end and capped at an opposite end. The second tube surrounds the first tube. The first gas volume is formed by one of an interior region of the first tube and an annular region between the first and second tubes. The second gas volume is formed by the other of the interior region of the first tube and the annular region between the first and second tubes.

In the second embodiments or any other disclosed embodiment, the reactor is a tubular reactor comprising a first tube and a second tube surrounding the first tube. The first gas volume is formed by one of an interior region of the first tube and an annular region between the first and second tubes. The second gas volume is formed by the other of the interior region of the first tube and the annular region between the first and second tubes.

In the second embodiments or any other disclosed embodiment, the membrane is formed on a surface of the first tube that is adjacent to the second volume.

In the second embodiments or any other disclosed embodiment, the first gas volume is formed by the interior region of the first tube, and the catalyst is disposed within or adjacent to the interior of the first tube. In the second embodiments or any other disclosed embodiment, the first gas volume is formed by the annular region between the first and second tubes, and the catalyst is disposed within or adjacent to an interior of the second tube. In the second embodiments or any other disclosed embodiment, the first gas volume is formed by the annular region between the first and second tubes, and the catalyst forms at least a portion of the second tube.

In the second embodiments or any other disclosed embodiment, the device further includes an inlet tube disposed to communicate a feed gas flow to the first gas volume. In the second embodiments or any other disclosed embodiment, the first gas volume is formed by the interior region of the first tube, and the catalyst forms at least a portion of the inlet tube. In the second embodiments or any other disclosed embodiment, the first gas volume is formed by the annular region between the first and second tubes, and the catalyst forms at least a portion of the inlet tube.

In the second embodiments or any other disclosed embodiment, the device further includes a controller that regulates operation of the reactor to change a percentage of methane converted by the device and/or a selectivity of the methane conversion to one or more products. In the second embodiments or any other disclosed embodiment, in regulating operation of the reactor, the controller can control one or more of reactor temperature, gas flow rates, gas concentration, and gas compositions.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The foregoing descriptions apply, in some cases, to examples generated in a laboratory, but these examples can be extended to production techniques. Thus, where quantities and techniques apply to the laboratory examples, they should not be understood as limiting. Moreover, although terms such as annular, tubular, and tube have been used herein, embodiments of the disclosed subject matter are not limited to a circular cross-sectional geometry. Indeed, other cross-sectional geometries besides circular are also contemplated.

It is thus apparent that there is provided, in accordance with the present disclosure, systems, methods, and devices for methane conversion. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method of converting methane, the method comprising:
    flowing methane in a first volume so as to contact a catalyst in a reactor while heating the reactor to an elevated temperature;
    transporting $H_2$ from the first volume to a second volume in the reactor via a membrane supported within the reactor; and
    removing products from the first volume,
    wherein the products comprise $C_2$ hydrocarbons and/or aromatics,
    a composition of the catalyst is selected such that the catalyst catalyzes conversion of methane into said products at a same operating temperature at which the membrane transports $H_2$,
    the membrane comprises a perovskite-type oxide having a formula of $M'Ce_{1-x-y}Zr_xM''_yO_{3-\delta}$, where:
    M' is a least one of Sr and Ba;
    M'' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb;
    x is between 0.1 and 0.2, inclusive; and
    y is between 0.1 and 0.3, inclusive,
    the catalyst comprises Fe(c)$SiO_2$,
    the method further comprises forming the catalyst by fusing ferrous metasilicate with quartz, and
    the ferrous metasilicate is formed by a sol-gel method employing a mixture of toluene, methanol, $FeCl_2$, $NaOC_2H_5$, tetraethyl orthosilicate (TEOS), and NaOH.

2. The method of claim 1, wherein the membrane is disposed on a surface of a porous support, the porous support comprising a material different than the membrane, and the membrane and the porous support have coefficients of thermal expansion that are substantially the same.

3. The method of claim 2, wherein the porous support comprises a perovskite-type oxide having a formula of $M'Ce_{1-x}Zr_xO_{3-\delta}$, where M' is Sr or Ba, and x is between 0.1 and 0.3, inclusive.

4. The method of claim 1, wherein the transporting $H_2$ through the membrane is via ion transport without an externally applied electric field.

5. The method of claim 1, further comprising, at a same time as the flowing a reactant gas, flowing a sweep gas in the second volume to remove the transported $H_2$ therefrom and/or to react with the transported $H_2$ therein.

6. The method of claim 5, wherein the sweep gas includes $H_2$ and further comprising adjusting an amount of $H_2$ in the sweep gas to regulate a selectivity of the methane conversion to one or more of the products.

7. The method of claim 5, further comprising adjusting a flow rate of the sweep gas to regulate a percentage of methane converted and/or a selectivity of the methane conversion to one or more of the products.

8. The method of claim 5, further comprising:
    reacting the transported $H_2$ with the sweep gas to form a secondary product; and
    heating the reactor using heat from the reaction between the transported $H_2$ and the sweep gas,
    wherein the sweep gas comprises air or steam, and
    the secondary product comprises water.

9. The method of claim 5, further comprising:
    reacting the transported $H_2$ with the sweep gas to form a secondary product,
    wherein the sweep gas comprises $CO_2$ or CO, and
    the secondary product comprises syngas, methanol, dimethyl ether, higher alcohols, and/or additional hydrocarbons.

10. The method of claim 9, wherein the transported $H_2$ in the second volume contacts a second catalyst comprising at least one of Ni, Fe, Cu, Zn, and a metal oxide support.

11. The method of claim 1, wherein one or more gases in addition to methane are flowed into the first volume and further comprising:
    adjusting a partial pressure of the one or more gases to regulate a percentage of methane converted and/or a selectivity of the methane conversion to one or more of the products,
    wherein the one or more gases comprises at least one of $H_2$, $C_2H_2$, $C_2H_4$, $C_2H_6$, and higher hydrocarbons and aromatics.

12. The method of claim 1, further comprising at least one of:
    adjusting a space velocity of the methane flow in the first volume to regulate a percentage of methane converted, and
    adjusting a partial pressure of the methane flow in the first volume to regulate a selectivity of the methane conversion to one or more of the products.

13. The method of claim 1, wherein the reactor comprises an inner support tube and an outer tube surrounding the inner support tube, the first volume being one of an interior of the inner support tube and an annular volume between the inner and outer tubes, the second volume being the other of the interior of the inner support tube and the annular volume between the inner and outer tubes.

14. The method of claim 13,
    wherein the first volume is the interior of the inner support tube, and the membrane is disposed on an outer surface of the inner support tube, and at least a portion of the interior of the inner support tube is packed with the catalyst.

15. The method of claim 13,
wherein the first volume is the annular volume between the inner and outer tubes, and the membrane is disposed on an inner surface of the inner support tube,
at least a portion of an interior of the outer tube is packed with the catalyst or at least a portion of the outer tube is formed of the catalyst.

16. The method of claim 1,
wherein the reactor comprises an inner support tube, an inlet tube having an outlet within the inner support tube, and an outer tube surrounding the inner support tube,
the first volume being one of an interior of the inner support tube and an annular volume between the inner and outer tubes,
the second volume being the other of the interior of the inner support tube and the annular volume between the inner and outer tubes,
the membrane is disposed on a surface of the inner support tube adjacent to the second volume, and
at least a portion of the inlet tube is formed of the catalyst and the first volume is the interior of the inner support, or at least at portion of the outer tube is formed of the catalyst and the first volume is the annular volume between the inner and outer tubes.

17. The method of claim 1, further comprising providing the reactor,
wherein the membrane of the reactor is formed by a process comprising:
forming a powder via a citrate precipitation method;
forming a paste from the powder;
applying the paste to a support; and
sintering the support, and
wherein the forming a paste comprises:
ball milling the powder with a solvent;
combining the ball-milled powder with an ester-alcohol based material that includes a binder and a plasticizer;
evaporating the solvent to form the paste.

18. The method of claim 1, further comprising providing the reactor,
wherein the membrane of the reactor is formed by a process comprising:
forming a powder via a citrate precipitation method;
forming a paste from the powder;
applying the paste to a support; and
sintering the support, and
wherein the applying the paste to a support comprises:
diluting the paste in a solvent;
coating the support in the diluted paste; and
drying the coated support.

19. The method of claim 18, wherein the coating and drying are performed more than once to provide a multilayer coating forming the membrane.

20. The method of claim 1, wherein the flow into the first volume consists essentially of methane.

21. The method of claim 1, wherein said operating temperature is at least 1000° C.

22. A method of converting methane, the method comprising:
flowing methane in a first volume so as to contact a catalyst in a reactor while heating the reactor to an elevated temperature;
transporting $H_2$ from the first volume to a second volume in the reactor via a membrane supported within the reactor; and
removing products from the first volume,
wherein the products comprise $C_2$ hydrocarbons and/or aromatics,
a composition of the catalyst is selected such that the catalyst catalyzes conversion of methane into said products at a same operating temperature at which the membrane transports $H_2$,
the membrane comprises a perovskite-type oxide having a formula of $M'Ce_{1-x-y}Zr_xM''_yO_{3-\delta}$, where:
M' is a least one of Sr and Ba;
M" is at least one of Ti, V, Cr, Mn, Fe, Co Ni, Cu, Nb, Mo, W, Pr, Nd, Pm, Sm, Eu, Gd, Tb, Dy, Ho, Er, Tm and Yb;
x is between 0.1 and 0.2, inclusive; and
y is between 0.1 and 0.3, inclusive,
the method further comprises providing the reactor, and
wherein the membrane of the reactor is formed by a process comprising:
forming a powder via a citrate precipitation method;
forming a paste from the powder;
applying the paste to a support; and
sintering the support, and wherein the forming a powder comprises:
dissolving in solution stoichiometric amounts of $Ce(NO_3)_3 \cdot 6H_2O$, $Sr(NO_3)$, $ZrO(NO_3)_2 \cdot H_2O$, and $Eu(NO_3)_3 \cdot 6H_2O$;
adding citric acid and ethylene glycol to the solution;
heating to a first temperature to evaporate solvent from the solution so as to form a gel;
heating to a second temperature greater than the first temperature to combust the gel;
ball milling the combusted gel followed by drying and grinding; and
heating to a third temperature greater than the second temperature to form a ceramic.

23. The method of claim 22, wherein the catalyst comprises $Fe(c)SiO_2$.

24. The method of claim 23, further comprising forming the catalyst by fusing ferrous metasilicate with quartz, wherein the ferrous metasilicate is formed by a sol-gel method employing a mixture of toluene, methanol, $FeCl_2$, $NaOC_2H_5$, tetraethyl orthosilicate (TEOS), and NaOH.

* * * * *